US006987102B2

(12) United States Patent
Bridger et al.

(10) Patent No.: US 6,987,102 B2
(45) Date of Patent: Jan. 17, 2006

(54) METHODS TO MOBILIZE PROGENITOR/STEM CELLS

(75) Inventors: Gary J. Bridger, Bellingham, WA (US); Michael J. Abrams, Custer, WA (US); Geoffrey W. Henson, Ferndale, WA (US); Ronald Trevor MacFarland, Vancouver (CA); Gary B. Calandra, Cresco, PA (US); Hal E. Broxmeyer, Indianapolis, IN (US); David C. Dale, Seattle, WA (US)

(73) Assignee: Anormed, Inc., Langley (CA)

( * ) Notice: Subject to any disclaimer, the term of this patent is extended or adjusted under 35 U.S.C. 154(b) by 357 days.

(21) Appl. No.: 10/209,001

(22) Filed: Jul. 30, 2002

(65) Prior Publication Data

US 2003/0130250 A1 Jul. 10, 2003

Related U.S. Application Data

(60) Provisional application No. 60/309,196, filed on Jul. 31, 2001, provisional application No. 60/382,155, filed on May 20, 2002.

(51) Int. Cl.
*A61K 31/33* (2006.01)
*C07D 245/00* (2006.01)
*C07D 487/00* (2006.01)

(52) U.S. Cl. ........................ 514/183; 540/473; 540/474
(58) Field of Classification Search ................ 514/183; 540/473, 474
See application file for complete search history.

(56) References Cited

U.S. PATENT DOCUMENTS

| | | | |
|---|---|---|---|
| 5,021,409 A | 6/1991 | Murrer et al. | 514/183 |
| 5,582,823 A | 12/1996 | Souza | 424/85.2 |
| 5,583,131 A | 12/1996 | Bridger et al. | 514/183 |
| 5,606,053 A | 2/1997 | Prashad et al. | 540/474 |
| 5,612,478 A | 3/1997 | Xu et al. | 540/474 |
| 5,698,546 A | 12/1997 | Bridger et al. | 514/183 |
| 5,756,728 A | 5/1998 | Xu et al. | 540/474 |
| 5,801,281 A | 9/1998 | Xu et al. | 564/82 |
| 5,817,807 A | 10/1998 | Bridger et al. | 540/474 |
| 6,001,826 A | 12/1999 | Murrer et al. | 514/183 |
| 6,365,583 B1 * | 4/2002 | MacFarland et al. | 514/183 |
| 6,667,320 B2 * | 12/2003 | Bridger et al. | 514/336 |
| 6,670,354 B2 * | 12/2003 | MacFarland et al. | 514/183 |
| 2002/0058653 A1 * | 5/2002 | MacFarland et al. | 514/183 |
| 2004/0102428 A1 * | 5/2004 | Bridger et al. | 514/183 |

FOREIGN PATENT DOCUMENTS

| | | |
|---|---|---|
| WO | WO 00/02870 | 1/2000 |
| WO | WO 00/45814 * | 8/2000 |
| WO | WO 00/56729 | 9/2000 |
| WO | WO 01/44229 | 6/2001 |
| WO | WO 02/22599 | 3/2002 |
| WO | WO 02/22600 | 3/2002 |
| WO | WO 02/26721 | 4/2002 |
| WO | WO 02/34745 | 5/2002 |
| WO | WO 02/58653 | 8/2002 |

OTHER PUBLICATIONS

Moore et al., 2001, Ann. N.Y. Acad. Sci. vol. 938, pp. 36-45.*
AM Smits, et al. J. Cell. Mol. Med. (2005) 9(1), pp. 25-36.*
J. Finer. "Mass. Senate passes stem cell bill . . . " Washington Post, Mar. 31, 2005, p. A2. 2 pages.*
S. Burdach. Klin. Pädiatr. 1991. pp. 302-310.*
J. DiJulio. Oncol. Nurs. Forum. 1991. pp. 3-6.*
C. Szabó, et al. Brit. J. Pharm. (1998), 125, pp. 379-387.*
WK Purves, et al. Life: the science of biology. 1992. pp. 928-929.*
C.W. Hendrix, et al. Antimicrob. Agents Chemother. 2000. pp. 1667-1673.*
M. Witvrouw, et al. Antiviral Chem. Chemother. (1996) 7(1), pp. 27-30.*
CAS Registry Number 155148-31-5. Accessed Apr. 1, 2005. 1 page.*
JM3100. ChemIDplus Lite. Accessed Apr. 1, 2005. 1 page.*
1,1'-1,4-phenylenebis(methylene)bis[1,4,8,11-tetraazacyclotetradecane]. NIAID Chemical Compound Search. Accessed Apr. 1, 2005. 1 page.*

* cited by examiner

*Primary Examiner*—Bruce R. Campell
*Assistant Examiner*—Andrew D. Kosar
(74) *Attorney, Agent, or Firm*—Morrison & Foerster LLP

(57) ABSTRACT

Certain nitrogen-containing compounds that bind the chemokine receptor CXCR4 are able to mobilize progenitor and/or stem cells into the peripheral blood to permit harvesting them for stem cell transplantation.

22 Claims, 1 Drawing Sheet a = P-value compared to Control/Saline
b = P-value compared to G-CSF/Saline
c = P-value compared to Control/MIP-1α+AMD3100

METHODS TO MOBILIZE PROGENITOR/STEM CELLS

CROSS-REFERENCE TO RELATED APPLICATIONS

This application claims priority under 35 U.S.C. § 119 (e) to U.S. provisional application Ser. No. 60/309,196 filed 31 Jul. 2001 and to U.S. provisional application Ser. No. 60/382,155 filed 20 May 2002. The contents of these applications are incorporated herein by reference.

TECHNICAL FIELD

The invention is in the field of therapeutics and medicinal chemistry. More particularly, the invention concerns methods to mobilize progenitor/stem cells in subjects by administering certain polyamines.

BACKGROUND ART

Blood cells play a crucial part in maintaining the health and viability of animals, including humans. White blood cells include neutrophils, macrophage, eosinophils and basophils/mast cells as well the B and T cells of the immune system. White blood cells are continuously replaced via the hematopoietic system, by the action of colony stimulating factors (CSF) and various cytokines on stem cells and progenitor cells in hematopoietic tissues. The nucleotide sequences encoding a number of these growth factors have been cloned and sequenced. Perhaps the most widely known of these is granulocyte colony stimulating factor (G-CSF) which has been approved for use in counteracting the negative effects of chemotherapy by stimulating the production of white blood cells and progenitor cells (peripheral blood stem cell mobilization). A discussion of the hematopoietic effects of this factor can be found, for example, in U.S. Pat. No. 5,582,823, incorporated herein by reference.

Several other factors have been reported to increase white blood cells and progenitor cells in both human and animal subjects. These agents include granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin and growth related oncogene, as single agents or in combination (Dale, D., et al., *Am. J. of Hematol.* (1998) 57:7–15; Rosenfeld, C., et al., *Bone Marrow Transplantation* (1997) 17:179–183; Pruijt, J., et al., *Cur. Op. in Hematol.* (1999) 6:152–158; Broxmeyer, H., et al., *Exp. Hematol.* (1995) 23:335–340; Broxmeyer, et al., *Blood Cells, Molecules and Diseases* (1998) 24:14–30; Glaspy, J., et al., *Cancer Chemother. Pharmacol.* (1996) 38 (suppl): S53–S57; Vadhan-Raj, S., et al., *Ann. Intern. Med.* (1997) 126:673–81; King, A., et al., *Blood* (2001) 97:1534–1542; Glaspy, J., et al., *Blood* (1997) 90:2939–2951).

While endogenous growth factors are pharmacologically effective, the well known disadvantages of employing proteins and peptides as pharmaceuticals underlies the need to add to the repertoire of such growth factors with agents that are small molecules. In another aspect, such small molecules are advantageous over proteins and peptides where production in large quantities are desired.

A number of cyclic polyamine antiviral agents have been described in a series of U.S. patents and applications over the last several years. These patents, U.S. Pat. Nos. 5,021,409; 6,001,826; 5,583,131; 5,698,546; and 5,817,807 are incorporated herein by reference. Also incorporated by reference are PCT publications WO 00/02870 based on an application filed 8 Jul. 1998 and WO 01/44229, based on an application filed 17 Dec. 1999, which describe additional compounds. These publications describe the structural characteristics of the cyclic polyamine antiviral agents.

The structural characteristics of a number of non-cyclic amine antiviral agents have also been described in a series of U.S. applications, now published as PCT publications. These publications, WO 00/56729, based on an application filed 24 Mar. 2000; WO 02/22600, based on applications filed 15 and 20 Sep. 2000; WO 02/22599, based on applications filed 15 and 22 Sep. 2000 as well as WO 02/34745 published 2 May 2002, are incorporated herein by reference in their entirety.

In addition, improved methods for preparation of some of the cyclic polyamine compounds are described in U.S. Pat. Nos. 5,612,478; 5,756,728; 5,801,281; and 5,606,053 and PCT publication WO 02/26721, based on an application filed 29 Sep. 2000. The disclosures of these U.S. documents are also incorporated herein by reference in their entirety.

We have previously found, and have disclosed in PCT publication WO 02/58653, based on an application filed 1 Feb. 2000, that some of the polyamine antiviral agents described in the above mentioned publications have the effect of increasing the white blood cell count. It has now been found that the polyamine antiviral agents described in the above-mentioned publications also have the effect of increasing progenitor cells and/or stem cells.

The development and maturation of blood cells is a complex process. Mature blood cells are derived from hematopoletic precursor cells (progenitor) cells and stem cells present in specific hematopoietic tissues including bone marrow. Within these environments hematopoietic cells proliferate and differentiate prior to entering the circulation. The chemokine receptor CXCR4 and its natural ligand stromal cell derived factor-1 (SDF-1) appear to be important in this process (for reviews see Maekawa, T., et al., *Internal Med.* (2000) 39:90–100; Nagasawa, T., et al., *Int. J. Hematol.* (2000) 72:408–411). This is demonstrated by reports that CXCR4 or SDF-1 knock-out mice exhibit hematopoietic defects (Ma, Q., et al., *Proc. Natl. Acad. Sci USA* (1998) 95:9448–9453; Tachibana, K., et al., *Nature* (1998) 393: 591–594; Zou, Y-R., et al., *Nature* (1998) 393:595–599) is also known that CD34+ progenitor cells express CXCR4 and require SDF-1 produced by bone marrow stromal cells for chemoattraction and engraftment (Peled, A., et al., *Science* (1999) 283:845–848) and that in vitro, SDF-1 is chemotactic for both CD34+ cells (Aiuti, A., et al., *J. Exp. Med.* (1997) 185:111–120; Viardot, A., et al., *Ann. Hematol.* (1998) 77:194–197) and for progenitor/stem cells (Jo, D-Y., et al., *J. Clin. Invest.* (2000) 105: 101–111). SDF-1 is also an important chemoattractant, signaling via the CXCR4 receptor, for several other more committed progenitors and mature blood cells including T-lymphocytes and monocytes (Bleul, C., et al., *J. Exp. Med.* (1996) 184:1101–1109), pro-and pre-B lymphocytes (Fedyk, E. R., et al., *J. Leukoc. Biol.* (1999) 66:667–673; Ma, Q., et al., *Immunity* (1999) 10:463–471) and megakaryocytes (Hodohara, K., et al., *Blood* (2000) 95:769–775; Riviere, C., et al., *Blood* (1999) 95:1511–1523; Majka, M., et al., *Blood* (2000) 96:4142–4151; Gear, A., et al., *Blood* (2001) 97:937–945; Abi-Younes, S., et al, *Circ. Res.* (2000) 86:131–138).

Thus, in summary, it appears that SDF-1 is able to control the positioning and differentiation of cells bearing CXCR4 receptors whether these cells are stem cells (i.e., cells which are CD34+) and/or progenitor cells (which result in formation of specified types of colonies in response to particular stimuli; that can be CD34+ or CD34− or cells that are somewhat more differentiated.

Recently, considerable attention has been focused on the number of CD34+ cells mobilized in the pool of peripheral blood progenitor cells used for autologous stem cell transplantation. The CD34+ population is the component thought to be primarily responsible for the improved recovery time after chemotherapy and the cells most likely responsible for long-term engraftment and restoration of hematopoiesis (Croop, J. M., et al., *Bone Marrow Transplantation* (2000) 26:1271–1279). The mechanism by which CD34+ cells re-engraft may be due to the chemotactic effects of SDF-1 on CXCR4 expressing cells (Voermans, C. Blood, 2001, 97, 799–804; Ponomaryov, T., et al., *J. Clin. Invest.* (2000) 106:1331–1339). More recently, adult hematopoietic stem cells were shown to be capable of restoring damaged cardiac tissue in mice (Jackson, K., et al., *J. Clin. Invest.* (2001) 107:1395–1402; Kocher, A., et al., *Nature Med.* (2001) 7:430–436).

Thus, the role of the CXCR4 receptor in managing cell positioning and differentiation has assumed considerable significance.

Citation of the above documents is not intended as an admission that any of the foregoing is pertinent prior art. All statements as to the date or representation as to the contents of these documents is based on the information available to the applicants and does not constitute any admission as to the correctness of the dates or contents of these documents. Further, all documents referred to throughout this application are incorporated in their entirety by reference herein.

DISCLOSURE OF THE INVENTION

The invention is directed to methods of treating animal subjects, in particular, veterinary and human subjects, to enhance the number of progenitor cells and/or stem cells. The progenitor and/or stem cells may be harvested and used in cell transplantation. The methods of the invention employ polyamines including those described in the patents and publications incorporated hereinabove by reference.

In one aspect, therefore, the invention is directed to a method to elevate the progenitor cells and/or stem cells, in a subject, which method comprises administering to said subject an amount of a compound of formula (1) or of a pharmaceutical composition thereof effective to elevate progenitor cell and/or stem cell levels. In one embodiment, bone marrow progenitor and/or stem cells are mobilized for myocardial repair.

The methods of the invention also include treatment of cell populations ex vivo with the compounds of formula (1) and introducing the treated populations into a compatible subject. The compounds of formula (1) may be used alone or in combination with other compounds and compositions to enhance the population of stem cells and/or progenitor cells in the peripheral blood. An enhanced production of white blood cells in the bone marrow may result as well.

In additional aspects, the invention is directed to pharmaceutical compositions containing the compound of formula (1) for use in effecting an elevation of progenitor cells and/or stem cells in animal subjects.

The compounds of formula (1) are of the formula:

Z-linker-Z'      (1)

wherein Z is a cyclic polyamine containing 9–32 ring members of which 2–8 are nitrogen atoms, said nitrogen atoms separated from each other by at least 2 carbon atoms, and wherein said heterocycle may optionally contain additional heteroatoms besides nitrogen and/or may be fused to an additional ring system;

or Z is of the formula

wherein A comprises a monocyclic or bicyclic fused ring system containing at least one N and B is H or an organic moiety of 1–20 atoms;

Z' may be embodied in a form as defined by Z above, or alternatively may be of the formula

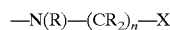

—N(R)—(CR$_2$)$_n$—X wherein each R is independently H or straight, branched or cyclic alkyl (1–6C), n is 1 or 2, and X is an aromatic ring, including heteroaromatic rings, or is a mercaptan;

"linker" represents a bond, alkylene (1–6C) or may comprise aryl, fused aryl, oxygen atoms contained in an alkylene chain, or may contain keto groups or nitrogen or sulfur atoms.

The preferred forms of the compounds of the invention are discussed below.

MODES OF CARRYING OUT THE INVENTION

Figure 1:
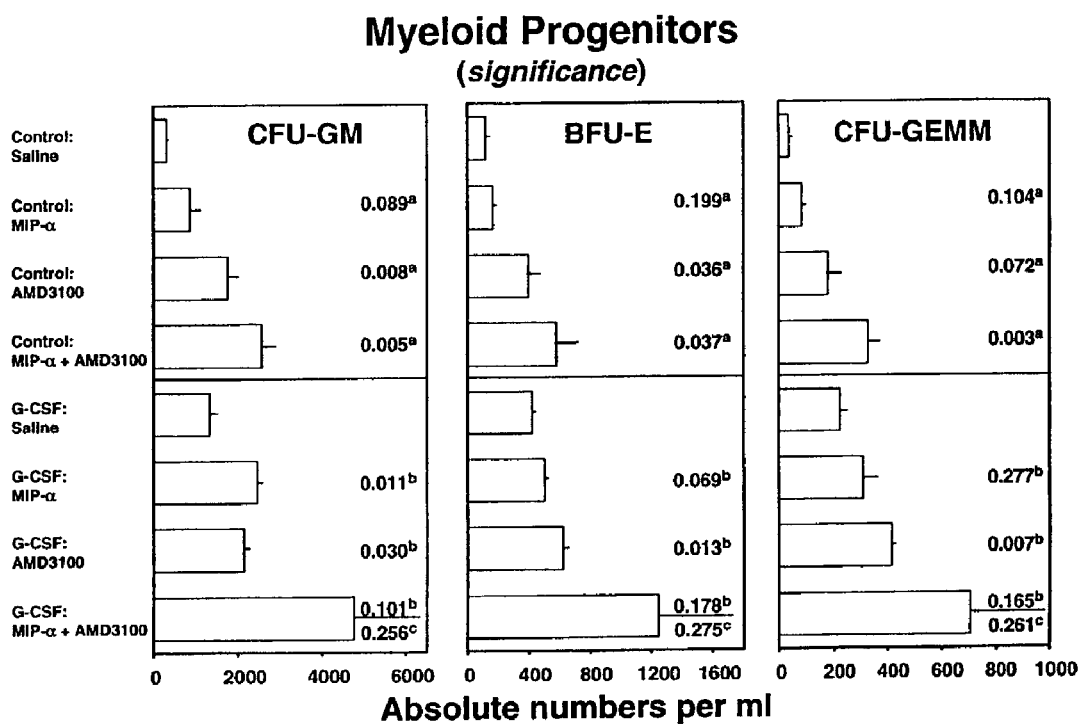
FIG. 1 shows a graph of obtaining myeloid progenitors in response to treatment with 1,1'-[1,4-phenylene-bis(methylene)]-bis-1,4,8,11-tetraazacyclotetradecane (AMD3100) in combination with macrophage inflammatory protein after administration of G-CSF.

The compounds useful in the invention are of the general formula set forth as formula (1) above. Certain embodiments are preferred; included among these are the compounds set forth in the above-incorporated U.S. patents and other patent documents.

The cyclic polyamine and non-cyclic amine antiviral agents described in the above-mentioned documents inhibit HIV replication via inhibition of CXCR4, the co-receptor required for fusion and entry of T-tropic HIV strains, and also inhibit the binding and signaling induced by the natural ligand, the chemokine SDF-1. While not wishing to be bound by any theory, the compounds of formula (1) which inhibit the binding of SDF-1 to CXCR4 effect an increase in stem and/or progenitor cells by virtue of such inhibition. Enhancing the stem and/or progenitor cells in blood is helpful in treatments to alleviate the effects of protocols that adversely affect the bone marrow, such as those that result in leukopenia. These are known side-effects of chemotherapy and radiotherapy. The compounds of formula (1) also enhance the success of bone marrow transplantation, enhance wound healing and burn treatment, and aid in restoration of damaged organ tissue. They also combat bacterial infections that are prevalent in leukemia. The compounds of formula (1) are used to mobilize and harvest CD34+ cells via apheresis with and without combinations with other mobilizing factors. The harvested cells are used in treatments requiring stem cell transplantations.

As used herein, the term "progenitor cells" refers to cells that, in response to certain stimuli, can form differentiated hematopoietic or myeloid cells. The presence of progenitor cells can be assessed by the ability of the cells in a sample to form colony-forming units of various types, including, for example, CFU-GM (colony-forming units, granulocyte-macrophage); CFU-GEMM (colony-forming units, multipotential); BFU-E (burst-forming units, erythroid); HPP-CFC (high proliferative potential colony-forming cells); or other types of differentiated colonies which can be obtained in culture using known protocols.

As used herein, "stem" cells are less differentiated forms of progenitor cells. Typically, such cells are often positive for CD34. Some stem cells do not contain this marker, however. These CD34+ cells can be assayed using fluorescence activated cell sorting (FACS) and thus their presence can be assessed in a sample using this technique.

In general, CD34+ cells are present only in low levels in the blood, but are present in large numbers in bone marrow. While other types of cells such as endothelial cells and mast cells also may exhibit this marker, CD34 is considered an index of stem cell presence.

In general, in compounds of formula (1), preferred embodiments of Z and Z' are cyclic polyamine moieties having from 9–24C that include 3–5 nitrogen atoms. Particularly preferred are 1,5,9,13-tetraazacyclohexadecane; 1,5,8,11,14-pentaazacyclohexadecane; 1,4,8,11-tetraazacyclotetradecane; 1,5,9-triazacyclododecane; 1,4,7,10-tetraazacyclododecane; and the like, including such cyclic polyamines which are fused to an additional aromatic or heteroaromatic rings and/or containing a heteroatom other than nitrogen incorporated in the ring. Embodiments wherein the cyclic polyamine contains a fused additional cyclic system or one or more additional heteroatoms are described in U.S. Pat. No. 5,698,546 and WO 01/44229 incorporated hereinabove by reference. Also preferred are 3,7,11,17-tetraazabicyclo(13.3.1)heptadeca-1(17),13,15-triene;
4,7,10,17-tetraazabicyclo(13.3.1)heptadeca-1(17),13,15-triene;
1,4,7,10-tetraazacyclotetradecane; 1,4,7-triazacyclotetradecane; and
4,7,10-triazabicyclo(13.3.1)heptadeca-1(17),13,15-triene.

When Z' is other than a cyclic polyamine as defined in Z, its preferred embodiments are set forth in U.S. Pat. No. 5,817,807, also incorporated herein by reference.

Preferred forms where
Z is of the formula

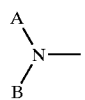

wherein A comprises a monocyclic or bicyclic fused ring system containing at least one N and B is H or an organic moiety of 1–20 atoms are disclosed in WO 00/56729; WO 02/22600; WO 02/34745; and WO 02/22599 cited above and all incorporated herein by reference.

Preferred forms of the linker moiety include those wherein the linker is a bond, or wherein the linker includes an aromatic moiety flanked by alkylene, preferably methylene moieties. Preferred linking groups include the methylene bracketed forms of 1,3-phenylene, 2,6-pyridine, 3,5-pyridine, 2,5-thiophene, 4,4'-(2,2'-bipyrimidine); 2,9-(1,10-phenanthroline) and the like. A particularly preferred linker is 1,4-phenylene-bis-(methylene).

Particularly preferred embodiments of the compound of the formula (1) include 2,2'-bicyclam; 6,6'-bicyclam; the embodiments set forth in U.S. Pat. Nos. 5,021,409, and 6,001,826, and in particular 1,1'-[1,4-phenylene-bis(methylene)]-bis-1,4,8,11-tetraazacyclotetradecane, set forth in U.S. Pat. No. 5,583,131, and designated herein AMD3100.

Other preferred embodiments include
N-[1,4,8,11-tetraazacyclotetradecanyl-1,4-phenylenebis(methylene)]-2-aminomethyl)pyridine;
7,7'-[1,4-phenylenebis(methylene)]bis-4,7,10,17-tetraazabicyclo-[13.3.1]heptadeca-1(17),13,15-triene;
7,7'-[1,4-phenylenebis(methylene)]bis-3,7,11,17-tetraazabicyclo[13.3.1]heptadeca-1(17),13,15-triene;
1,1'-[1,3-phenylenebis(methylene)]-bis-1,4,8,11-tetra-azacyclotetradecane;
1,1'-[1,4-phenylenebis(methylene)]-bis-1,4,8,11-tetra-azacyclotetradecane;
1,1'-[1,4-phenylene-bis-(methylene)]-bis-1,4,7,10-tetraazacyclotetradecane;
1,1'-[1,3-phenylene-bis-(methylene)]-bis-1,4,7,10-tetraazacyclotetradecane;
11,11'-(1,2-propanediyl)bis-1,4,8,11-tetraazacyclotetradecane;
N-[4-(1,4,7-triazacyclotetra-decane)-1,4-phenylenebis(methylene)]-2-(aminomethyl)pyridine;
N-[7-(4,7,10-triazabicyclo[13.3.1]heptadeca-1(17),13,15-triene)-1,4-phenylenebis(methylene)]-2-(aminomethyl)pyridine;
N-[7-(4,7,10,17-tetraazabicyclo[13.3.1]heptadeca-1(17),13,15-triene)-1,4-phenylenebis(methylene)]-2-(aminomethyl)pyridine;
N-[4-[4,7,10,17-tetraazabicyclo[13.3.1]heptadeca-1(17),13,15-triene]-1,4-phenylenebis(methylene)]-2-(aminomethyl)pyridine;
3,3'-(bis-1,5,9,13-tetraazacyclohexadecane); 3,3'-(bis-1,5,8,11,14-pentaazacyclohexadecane), methylene (or polymethylene) di-1-N-1,4,8,11-tetraazacyclotetradecane;
3,3'-bis-1,5,9,13,-tetraazacyclohexadecane;
3,3'-bis-1,5,8,11,14-pentaazacyclohexadecane;
5,5'-bis-1,4,8,11-tetraazacyclotetradecane;
2,5'-bis-1,4,8,11-tetraazacyclotetradecane;
2,6'-bis-1,4,8,11-tetraazacyclotetradecane;
11,11'-(1,2-ethanediyl)bis-1,4,8,11-tetraazacyclotetradecane;
11,11'-(1,2-propanediyl)bis-1,4,8,11-tetraazacyclotetradecane;
11,11'-(1,2-butanediyl)bis-1,4,8,11-tetraazacyclotetradecane;
11,11'-(1,2-pentanediyl)bis-1,4,8,11-tetraazacyclotetradecane;
11,11'-(1,2-hexanediyl)bis-1,4,8,11-tetraazacyclotetradecane;
3,3'-bis-1,5,9,13-tetraazacyclohexadecane;
3,3'-bis-1,5,8,11,14-pentaazacyclohexadecane;
5,5'-bis-1,4,8,11-tetraazacyclotetradecane;
2,5'-bis-1,4,8,11-tetraazacyclotetradecane;
2,6'-bis-1,4,8,11-tetraazacyclotetradecane;
11,11'-(1,2-ethanediyl)bis-1,4,8,11-tetraazacyclotetradecane;
11,11'-(1,2-propanediyl)bis-1,4,8,11-tetraazacyclotetradecane;

11,11'-(1,2-butanediyl)bis-1,4,8,11-tetraazacyclotetradecane;
11,11'-(1,2-pentanediyl)bis-1,4,8,11-tetraazacyclotetradecane;
11,11'-(1,2-hexanediyl)bis-1,4,8,11-tetraazacyclotetradecane;
1,1'-[1,3-phenylenebis(methylene)]-bis-1,4,8,11-tetra-azacyclotetradecane;
1,1'-[1,4-phenylenebis(methylene)]-bis-1,4,8,11-tetra-azacyclotetradecane;
1,1'-[3,3'-biphenylene-bis-(methylene)]-bis-1,4,8,11-tetraazacyclotetradecane;
11,11'-[1,4-phenylene-bis-(methylene)]-bis-1,4,7,11-tetraazacyclotetradecane;
1,11'-[1,4-phenylene-bis(methylene)]-1,4,8,11-tetraazacyclotetradecane;
1,1'-[2,6-pyridine-bis-(methylene)]-bis-1,4,8,11-tetraazacyclotetradecane;
1,1-[3,5-pyridine-bis-(methylene)]-bis-1,4,8,11-tetraazacyclotetradecane;
1,1'-[2,5-thiophene-bis-(methylene)]-bis-1,4,8,11-tetraazacyclotetradecane;
1,1'-[4,4'-(2,2'-bipyridine)-bis-(methylene)]-bis-1,4,8,11-tetraazacyclotetradecane;
1,1'-[2,9-(1,10-phenanthroline)-bis-(methylene)]-bis-1,4,8,11-tetraazacyclotetradecane;
1,1'-[1,3-phenylene-bis-(methylene)]-bis-1,4,7,10-tetraazacyclotetradecane;
1,1'-[1,4-phenylene-bis-(methylene)]-bis-1,4,7,10-tetraazacyclotetradecane;
1,1'-[5-nitro-1,3-phenylenebis(methylene)]bis-1,4,8,11-tetraazacyclotetradecane;
1,1'-[2,4,5,6-tetrachloro-1,3-phenyleneis(methylene)]bis-1,4,8,11-tetraazacyclotetradecane;
1,1'-[2,3,5,6-tetrafluoro-1,4-phenylenebis(methylene)]bis-1,4,8,11-tetraazacyclotetradecane;
1,1'-[1,4-naphthylene-bis-(methylene)]bis-1,4,8,11-tetraazacyclotetradecane;
1,1'-[1,3-phenylenebis-(methylene)]bis-1,5,9-triazacyclododecane;
1,1'-[1,4-phenylene-bis-(methylene)]-1,5,9-triazacyclododecane;
1,1'-[2,5-dimethyl-1,4-phenylenebis-(methylene)]-bis-1,4,8,11-tetraazacyclotetradecane;
1,1'-[2,5-dichloro-1,4-phenylenebis-(methylene)]-bis-1,4,8,11-tetraazacyclotetradecane;
1,1'-[2-bromo-1,4-phenylenebis-(methylene)]-bis-1,4,8,11-tetraazacyclotetradecane;
1,1'-[6-phenyl-2,4-pyridinebis-(methylene)]-bis-1,4,8,11-tetraazacyclotetradecane;
7,7'-[1,4-phenylene-bis(methylene)]bis-3,7,11,17-tetraazabicyclo[13.3.1]heptadeca-1(17),13,15-triene;
7,7'-[1,4-phenylene-bis(methylene)]bis[15-chloro-3,7,11,17-tetraazabicyclo[13.3.1]heptadeca-1(17),13,15-triene];
7,7'-[1,4-phenylene-bis(methylene)]bis[15-methoxy-3,7,11,17-tetraazabicyclo[13.3.1]heptadeca-1(17),13,15-triene];
7,7'-[1,4-phenylene-bis(methylene)]bis-3,7,11,17-tetraazabicyclo[13.3.1]-heptadeca-13,16-triene-15-one;
7,7'-[1,4-phenylene-bis(methylene)]bis-4,7,10,17-tetraazabicyclo[13.3.1]-heptadeca-1(17),13,15-triene;
8,8'-[1,4-phenylene-bis(methylene)]bis-4,8,12,19-tetraazabicyclo[15.3.1]nonadeca-1(19),15,17-triene;
6,6'-[1,4-phenylene-bis(methylene)]bis-3,6,9,15-tetraazabicyclo[11.3.1]pentadeca-1(15),11,13-triene;
6,6'-[1,3-phenylene-bis(methylene)]bis-3,6,9,15-tetraazabicyclo[11.3.1]pentadeca-1(15),11,13-triene;
17,17'-[1,4-phenylene-bis(methylene)]bis-3,6,14,17,23,24-hexaazatricyclo[17.3.1.1$^{8,12}$]tetracosa-1(23),8,10,12(24),19,21-hexaene;
N-[1,4,8,11-Tetraazacyclotetradecanyl-1,4-phenylenebis(methylene)]-2-(amino-methyl)pyridine;
N-[1,4,8,11-Tetraazacyclotetradecanyl-1,4-phenylenebis(methylene)]-N-methyl-2-(aminomethyl)pyridine;
N-[1,4,8,11-Tetraazacyclotetradecanyl-1,4-phenylenebis(methylene)]-4-)amino-methyl)pyridine;
N-[1,4,8,11-Tetraazacyclotetradecanyl-1,4-phenylenebis(methylene)]-3-(amino-methyl)pyridine;
N-[1,4,8,11-Tetraazacyclotetradecanyl-1,4-phenylenebis(methylene)]-(2-amino-methyl-5-methyl)pyrazine;
N-[1,4,8,11-Tetraazacyclotetradecanyl-1,4-phenylenebis(methylene)]-2-(amino-ethyl)pyridine;
N-[1,4,8,11-Tetraazacyclotetradecanyl-1,4-phenylenebis(methylene)]-2-(amino-methyl)thiophene;
N-[1,4,8,11-Tetraazacyclotetradecanyl-1,4-phenylenebis(methylene)]-2-(amino-ethyl)mercaptan;
N-[1,4,8,11-Tetraazacyclotetradecanyl-1,4-phenylenebis(methylene)]-2-amino-benzylamine;
N-[1,4,8,11-Tetraazacyclotetradecanyl-1,4-phenylenebis(methylene)]-4-amino-benzylamine;
N-[1,4,8,11-Tetraazacyclotetradecanyl-1,4-phenylenebis(methylene)]-4-(amino-ethyl)imidazole;
N-[1,4,8,11-Tetraazacyclotetradecanyl-1,4-phenylenebis(methylene)]-benzylamine;
N-[1,4,8,11-Tetraazacyclotetradecanyl-1,4-phenylenebis(methylene)]-purine;
N-[1,4,8,11-Tetraazacyclotetradecanyl-1,4-phenylenebis(methylene)]-4-phenylpiperazine;
N-[4-(1,4,7-Triazacyclotetra-decanyl)-1,4-phenylenebis(methylene)]-2-(aminomethyl)pyridine;
N-[7-(4,7,10,17-Tetraazabicyclo[13.3.1]heptadeca-1(17),13,15-trienyl)-1,4-phenylenebis(methylene)]-2-(aminomethyl)pyridine;
N-[7-(4,7,10-Triazabicyclo[13.3.1]heptadeca-1(17),13,15-trienyl)-1,4-phenylenebis(methylene)]-2-(aminomethyl)pyridine;
N-[4-[4,7,10-Triazabicyclo[13.3.1]heptadeca-1(17),13,15-trienyl]-1,4-phenylenebis(methylene)]-2-(aminomethyl)pyridine;
N-[1-(1,4,7-Triazacyclotetra-decanyl)-1,4-phenylenebis(methylene)]-2-(aminomethyl)pyridine;
N-[4-[4,7,10,17-Tetraazabicyclo[13.3.1]heptadeca-1(17),13,15-trienyl]-1,4-phenylenebis(methylene)]-2-(aminomethyl)pyridine;
N-[3-(3,6,17-Triazabicyclo[13.3.1]heptadeca-1(17),13,15-trienyl)-1,4-phenylenebis(methylene)]-2-(aminomethyl)pyridine;
N-[3-(3,6,17-Triazabicyclo[13.3.1]heptadeca-1(17),13,15-trienyl)-1,3-phenylenebis(methylene)]-2-(aminomethyl)pyridine;
N-[4-(4,7,17-Triazabicyclo[13.3.1]heptadeca-1(17),13,15-trienyl)-1,4-phenylenebis(methylene)]-2-(aminomethyl)pyridine;
N-[7-(4,7,17-Triazabicyclo[13.3.1]heptadeca-1(17),13,15-trienyl)-1,4-phenylenebis(methylene)]-2-(aminomethyl)pyridine;
N-[6-(3,6,9-Triazabicyclo[11.3.1]pentadeca-1(15),11,13-trienyl)-1,3-phenylenebis(methylene)]-2-(aminomethyl)pyridine;
N-[7-(4,10,17-Triazabicyclo[13.3.1]heptadeca-1(17),13,15-trienyl)-1,4-phenylenebis(methylene)]-2-(aminomethyl)pyridine;
N-[4-(1,7-Diazacyclotetradecanyl)-1,4-phenylenebis(methylene)]-2-(aminomethyl)pyridine;

N-[7-(4,10-Diazabicyclo[13.3.1]heptadeca-1(17),13,15-trienyl)-1,4-phenylenebis(methylene)]-2-(aminomethyl) pyridine;
N-[4-(11-Fluoro-1,4,7-triazacyclotetradecanyl)-1,4-phenylenebis(methylene)]-2-(aminomethyl)pyridine;
N-[4-(11,11-difluoro-1,4,7-triazacyclotetradecanyl)-1,4-phenylenebis(methylene)]-2-(aminomethyl)pyridine;
N-[4-(1,4,7-triazacyclotetradecan-2-one)-yl)]-1,4-phenylenebis(methylene)]-2-(aminomethyl)pyridine;
N-[12-(5-oxa-1,9-diazacyclotetradecanyl)-1,4-phenylenebis(methylene)]-2-(aminomethyl)pyridine;
N-[4-(11-oxa-1,7-diazacyclotetradecanyl)-1,4-phenylenebis(methylene)]-2-(aminomethyl)pyridine;
N-[4-(11-thia-1,7-diazacyclotetradecanyl)-1,4-phenylenebis(methylene)]-2-(aminomethyl)pyridine;
N-[4-(11-sulfoxo-1,7-diazacyclotetradecanyl)-1,4-phenylenebis(methylene)]-2-(aminomethyl)pyridine;
N-[4-(11-sulfono-1,7-diazacyclotetradecanyl)-1,4-phenylenebis(methylene)]-2-(aminomethyl)pyridine;
N-[4-(1,4,7-triazacyclotetradecan-3-one)-yl))-1,4-phenylenebis(methylene)]-2-(aminomethyl)pyridine;
N-(2-pyridinylmethyl)-N'-(6,7,8,9-tetrahydro-5H-cyclohepta[b]pyridin-9-yl)-1,4-benzenedimethanamine;
N-(2-pyridinylmethyl)-N'-(5,6,7,8-tetrahydro-8-quinolinyl)-1,4-benzenedimethanamine;
N-(2-pyridinylmethyl)-N'-(6,7-dihydro-5H-cyclopenta[b]pyridin-7-yl)-1,4-benzenedimethanamine;
N-(2-pyridinylmethyl)-N'-(1,2,3,4-tetrahydro-1-naphthalenyl)-1,4-benzenedimethanamine;
N-(2-pyridinylmethyl)-N'-(1-naphthalenyl)-1,4-benzenedimethanamine;
N-(2-pyridinylmethyl)-N'-(8-quinolinyl)-1,4-benzenedimethanamine;
N-(2-pyridinylmethyl)-N'-[2-[(2-pyridinylmethyl)amino]ethyl]-N'-(1-methyl-1,2,3,4-tetrahydro-8-quinolinyl)-1,4-benzene dimethanamine;
N-(2-pyridinylmethyl)-N'-[2-[(1H-imidazol-2-ylmethyl)amino]ethyl]-N'-(1-methyl-1,2,3,4-tetrahydro-8-quinolinyl)-1,4-benzene dimethanamine;
N-(2-pyridinylmethyl)-N'-(1,2,3,4-tetrahydro-8-quinolinyl)-1,4-benzenedimethanamine;
N-(2-pyridinylmethyl)-N'-[2-[(1H-imidazol-2-ylmethyl)amino]ethyl]-N'-(1,2,3,4-tetrahydro-1-naphthalenyl)-1,4-benzene dimethanamine;
N-(2-pyridinylmethyl)-N'-(2-phenyl-5,6,7,8-tetrahydro-8-quinolinyl)-1,4-benzenedimethanamine;
N,N'-bis(2-pyridinylmethyl)-N'-(2-phenyl-5,6,7,8-tetrahydro-8-quinolinyl)-1,4-benzenedimethanamine;
N-(2-pyridinylmethyl)-N'-(5,6,7,8-tetrahydro-5-quinolinyl)-1,4-benzenedimethanamine;
N-(2-pyridinylmethyl)-N'-(1H-imidazol-2-ylmethyl)-N'-(5,6,7,8-tetrahydro-5-quinolinyl)-1,4-benzenedimethanamine;
N-(2-pyridinylmethyl)-N'-(1H-imidazol-2-ylmethyl)-N'-(5,6,7,8-tetrahydro-8-quinolinyl)-1,4-benzenedimethanamine;
N-(2-pyridinylmethyl)-N'-[(2-amino-3-phenyl)propyl]-N'-(5,6,7,8-tetrahydro-8-quinolinyl)-1,4-benzenedimethanamine;
N-(2-pyridinylmethyl)-N'-(1H-imidazol-4-ylmethyl)-N'-(5,6,7,8-tetrahydro-8-quinolinyl)-1,4-benzenedimethanamine;
N-(2-pyridinylmethyl)-N'-(2-quinolinylmethyl)-N'-(5,6,7,8-tetrahydro-8-quinolinyl)-1,4-benzenedimethanamine;
N-(2-pyridinylmethyl)-N'-(2-(2-naphthoyl)aminoethyl)-N'-(5,6,7,8-tetrahydro-8-quinolinyl)-1,4-benzenedimethanamine;
N-(2-pyridinylmethyl)-N'-[(S)-(2-acetylamino-3-phenyl)propyl]-N'-(5,6,7,8-tetrahydro-8-quinolinyl)-1,4-benzenedimethanamine;
N-(2-pyridinylmethyl)-N'-[(S)-(2-acetylamino-3-phenyl)propyl]-N'-(5,6,7,8-tetrahydro-8-quinolinyl)-1,4-benzenedimethanamine;
N-(2-pyridinylmethyl)-N'-[3-((2-naphthalenylmethyl)amino)propyl]-N'-(5,6,7,8-tetrahydro-8-quinolinyl)-1,4-benzenedimethanamine;
N-(2-pyridinylmethyl)-N'-[2-(S)-pyrollidinylmethyl]-N'-(5,6,7,8-tetrahydro-8-quinolinyl)-1,4-benzenedimethanamine;
N-(2-pyridinylmethyl)-N'-[2-(R)-pyrollidinylmethyl]-N'-(5,6,7,8-tetrahydro-8-quinolinyl)-1,4-benzenedimethanamine;
N-(2-pyridinylmethyl)-N'-[3-pyrazolylmethyl]-N'-(5,6,7,8-tetrahydro-8-quinolinyl)-1,4-benzenedimethanamine;
N-(2-pyridinylmethyl)-N'-[2-pyrrolylmethyl]-N'-(5,6,7,8-tetrahydro-8-quinolinyl)-1,4-benzenedimethanamine;
N-(2-pyridinylmethyl)-N'-[2-thiopheneylmethyl]-N'-(5,6,7,8-tetrahydro-8-quinolinyl)-1,4-benzenedimethanamine
N-(2-pyridinylmethyl)-N'-[2-thiazolylmethyl]-N'-(5,6,7,8-tetrahydro-8-quinolinyl)-1,4-benzenedimethanamine;
N-(2-pyridinylmethyl)-N'-[2-furanylmethyl]-N'-(5,6,7,8-tetrahydro-8-quinolinyl)-1,4-benzenedimethanamine;
N-(2-pyridinylmethyl)-N'-[2-[(phenylmethyl)amino]ethyl]-N'-(5,6,7,8-tetrahydro-8-quinolinyl)-1,4-benzenedimethanamine;
N-(2-pyridinylmethyl)-N'-(2-aminoethyl)-N'-(5,6,7,8-tetrahydro-8-quinolinyl)-1,4-benzenedimethanamine;
N-(2-pyridinylmethyl)-N'-3-pyrrolidinyl-N'-(5,6,7,8-tetrahydro-8-quinolinyl)-1,4-benzenedimethanamine
N-(2-pyridinylmethyl)-N'-4-piperidinyl-N'-(5,6,7,8-tetrahydro-8-quinolinyl)-1,4-benzenedimethanamine;
N-(2-pyridinylmethyl)-N'-[2-[(phenyl)amino]ethyl]-N'-(5,6,7,8-tetrahydro-8-quinolinyl)-1,4-benzenedimethanamine;
N-(2-pyridinylmethyl)-N'-(7-methoxy-1,2,3,4-tetrahydro-2-naphthalenyl)-1,4-benzenedimethanamine;
N-(2-pyridinylmethyl)-N'-(6-methoxy-1,2,3,4-tetrahydro-2-naphthalenyl)-1,4-benzenedimethanamine;
N-(2-pyridinylmethyl)-N'-(1-methyl-1,2,3,4-tetrahydro-2-naphthalenyl)-1,4-benzenedimethanamine;
N-(2-pyridinylmethyl)-N'-(7-methoxy-3,4-dihydronaphthalenyl)-1-(aminomethyl)-4-benzamide;
N-(2-pyridinylmethyl)-N'-(6-methoxy-3,4-dihydronaphthalenyl)-1-(aminomethyl)-4-benzamide;
N-(2-pyridinylmethyl)-N'-(1H-imidazol-2-ylmethyl)-N'-(7-methoxy-1,2,3,4-tetrahydro-2-naphthalenyl)-1,4-benzenedimethanamine;
N-(2-pyridinylmethyl)-N'-(8-hydroxy-1,2,3,4-tetrahydro-2-naphthalenyl)-1,4-benzenedimethanamine;
N-(2-pyridinylmethyl)-N'-(1H-imidazol-2-ylmethyl)-N'-(8-hydroxy-1,2,3,4-tetrahydro-2-naphthalenyl)-1,4-benzenedimethanamine;
N-(2-pyridinylmethyl)-N'-(8-Fluoro-1,2,3,4-tetrahydro-2-naphthalenyl)-1,4-benzenedimethanamine;
N-(2-pyridinylmethyl)-N'-(1H-imidazol-2-ylmethyl)-N'-(8-Fluoro-1,2,3,4-tetrahydro-2-naphthalenyl)-1,4-benzenedimethanamine;
N-(2-pyridinylmethyl)-N'-(5,6,7,8-tetrahydro-7-quinolinyl)-1,4-benzenedimethanamine;
N-(2-pyridinylmethyl)-N'-(1H-imidazol-2-ylmethyl)-N'-(5,6,7,8-tetrahydro-7-quinolinyl)-1,4-benzenedimethanamine;

N-(2-pyridinylmethyl)-N'-[2-[(2-naphthalenylmethyl) amino]ethyl]-N'-(5,6,7,8-tetrahydro-8-quinolinyl)-1,4-benzenedimethanamine;

N-(2-pyridinylmethyl)-N'-[2-(isobutylamino)ethyl]-N'-(5,6,7,8-tetrahydro-8-quinolinyl)-1,4-benzenedimethanamine;

N-(2-pyridinylmethyl)-N'-[2-[(2-pyridinylmethyl)amino] ethyl]-N'-(5,6,7,8-tetrahydro-8-quinolinyl)-1,4-benzenedimethanamine;

N-(2-pyridinylmethyl)-N'-[2-[(2-furanylmethyl)amino] ethyl]-N'-(5,6,7,8-tetrahydro-8-quinolinyl)-1,4-benzenedimethanamine;

N-(2-pyridinylmethyl)-N'-(2-guanidinoethyl)-N'-(5,6,7,8-tetrahydro-8-quinolinyl)-1,4-benzenedimethanamine;

N-(2-pyridinylmethyl)-N'-[2-[bis-[(2-methoxy)phenylmethyl]amino]ethyl]-N'-(5,6,7,8-tetrahydro-8-quinolinyl)-1,4-benzene dimethanamine;

N-(2-pyridinylmethyl)-N'-[2-[(1H-imidazol-4-ylmethyl)amino]ethyl]-N'-(5,6,7,8-tetrahydro-8-quinolinyl)-1,4-benzene dimethanamine;

N-(2-pyridinylmethyl)-N'-[2-[(1H-imidazol-2-ylmethyl)amino]ethyl]-N'-(5,6,7,8-tetrahydro-8-quinolinyl)-1,4-benzenedimethanamine;

N-(2-pyridinylmethyl)-N'-[2-(phenylureido)ethyl]-N'-(5,6,7,8-tetrahydro-8-quinolinyl)-1,4-benzenedimethanamine;

N-(2-pyridinylmethyl)-N'-[[N"-(n-butyl)carboxamido]methyl]-N'-(5,6,7,8-tetrahydro-8-quinolinyl)-1,4-benzenedimethanamine;

N-(2-pyridinylmethyl)-N'-(carboxamidomethyl)-N'-(5,6,7,8-tetrahydro-8-quinolinyl)-1,4-benzenedimethanamine;

N-(2-pyridinylmethyl)-N'-[(N"-phenyl)carboxamidomethyl]-N'-(5,6,7,8-tetrahydro-8-quinolinyl)-1,4-benzenedimethanamine;

N-(2-pyridinylmethyl)-N'-(carboxymethyl)-N'-(5,6,7,8-tetrahydro-8-quinolinyl)-1,4-benzenedimethanamine;

N-(2-pyridinylmethyl)-N'-(phenylmethyl)-N'-(5,6,7,8-tetrahydro-8-quinolinyl)-1,4-benzenedimethanamine;

N-(2-pyridinylmethyl)-N'-(1H-benzimidazol-2-ylmethyl)-N'-(5,6,7,8-tetrahydro-8-quinolinyl)-1,4-benzenedimethanamine;

N-(2-pyridinylmethyl)-N'-(5,6-dimethyl-1H-benzimidazol-2-ylmethyl)-N'-(5,6,7,8-tetrahydro-8-quinolinyl)-1,4-benzenedimethanamine (hydrobromide salt);

N-(2-pyridinylmethyl)-N'-(5-nitro-1H-benzimidazol-2-ylmethyl)-N'-(5,6,7,8-tetrahydro-8-quinolinyl)-1,4-benzenedimethanamine;

N-(2-pyridinylmethyl)-N'-[(1H)-5-azabenzimidazol-2-ylmethyl]-N'-(5,6,7,8-tetrahydro-8-quinolinyl)-1,4-benzenedimethanamine;

N-(2-pyridinylmethyl)-N-(4-phenyl-1H-imidazol-2-ylmethyl)-N'-(5,6,7,8-tetrahydro-8-quinolinyl)-1,4-benzenedimethanamine;

N-(2-pyridinylmethyl)-N'-[2-(2-pyridinyl)ethyl]-N'-(5,6,7,8-tetrahydro-8-quinolinyl)-1,4-benzenedimethanamine;

N-(2-pyridinylmethyl)-N'-(2-benzoxazolyl)-N'-(5,6,7,8-tetrahydro-8-quinolinyl)-1,4-benzenedimethanamine;

N-(2-pyridinylmethyl)-N'-(trans-2-aminocyclohexyl)-N'-(5,6,7,8-tetrahydro-8-quinolinyl)-1,4-benzenedimethanamine;

N-(2-pyridinylmethyl)-N'-(2-phenylethyl)-N'-(5,6,7,8-tetrahydro-8-quinolinyl)-1,4-benzenedimethanamine;

N-(2-pyridinylmethyl)-N'-(3-phenylpropyl)-N'-(5,6,7,8-tetrahydro-8-quinolinyl)-1,4-benzenedimethanamine;

N-(2-pyridinylmethyl)-N'-(trans-2-aminocyclopentyl)-N'-(5,6,7,8-tetrahydro-8-quinolinyl)-1,4-benzenedimethanamine;

N-[[4-[[(2-pyridinylmethyl)amino]methyl]phenyl]methyl]-N-(5,6,7,8-tetrahydro-8-quinolinyl)-glycinamide;

N-[[4-[[(2-pyridinylmethyl)amino]methyl]phenyl]methyl]-N-(5,6,7,8-tetrahydro-8-quinolinyl)-(L)-alaninamide;

N-[[4-[[(2-pyridinylmethyl)amino]methyl]phenyl]methyl]-N-(5,6,7,8-tetrahydro-8-quinolinyl)-(L)-aspartamide;

N-[[4-[[(2-pyridinylmethyl)amino]methyl]phenyl]methyl]-N-(5,6,7,8-tetrahydro-8-quinolinyl)-pyrazinamide;

N-[[4-[[(2-pyridinylmethyl)amino]methyl]phenyl]methyl]-N-(5,6,7,8-tetrahydro-8-quinolinyl)-(L)-prolinamide;

N-[[4-[[(2-pyridinylmethyl)amino]methyl]phenyl]methyl]-N-(5,6,7,8-tetrahydro-8-quinolinyl)-(L)-lysinamide;

N-[[4-[[(2-pyridinylmethyl)amino]methyl]phenyl]methyl]-N-(5,6,7,8-tetrahydro-8-quinolinyl)-benzamide;

N-[[4-[[(2-pyridinylmethyl)amino]methyl]phenyl]methyl]-N-(5,6,7,8-tetrahydro-8-quinolinyl)-picolinamide;

N'-Benzyl-N-[[4-[[(2-pyridinylmethyl) amino]methyl]phenyl]methyl]-N-(5,6,7,8-tetrahydro-8-quinolinyl)-urea;

N'-phenyl-N-[[4-[[(2-pyridinylmethyl) amino]methyl]phenyl]methyl]-N-(5,6,7,8-tetrahydro-8-quinolinyl)-urea;

N-(6,7,8,9-tetrahydro-5H-cyclohepta[bacteriapyridin-9-yl)-4-[[(2-pyridinylmethyl)amino]methyl]benzamide;

N-(5,6,7,8-tetrahydro-8-quinolinyl)4-[[(2-pyridinylmethyl)amino]methyl]benzamide;

N,N'-bis(2-pyridinylmethyl)-N'-(5,6,7,8-tetrahydro-8-quinolinyl)-1,4-benzenedimethanamine;

N,N'-bis(2-pyridinylmethyl)-N'-(6,7,8,9-tetrahydro-5H-cyclohepta[bacteriapyridin-9-yl)-1,4-benzenedimethanamine;

N,N'-bis(2-pyridinylmethyl)-N'-(6,7-dihydro-5H-cyclopenta[bacteriapyridin-7-yl)-1,4-benzenedimethanamine;

N,N'-bis(2-pyridinylmethyl)-N'-(1,2,3,4-tetrahydro-1-naphthalenyl)-1,4-benzenedimethanamine;

N,N'-bis(2-pyridinylmethyl)-N'-[(5,6,7,8-tetrahydro-8-quinolinyl)methyl]-1,4-benzenedimethanamine;

N,N'-bis(2-pyridinylmethyl)-N'[(6,7-dihydro-5H-cyclopenta[bacteriapyridin-7-yl)methyl] -1,4-benzenedimethanamine;

N-(2-pyridinylmethyl)-N-(2-methoxyethyl)-N'-(5,6,7,8-tetrahydro-8-quinolinyl)-1,4-benzenedimethanamine;

N-(2-pyridinylmethyl)-N-[2-(4-methoxyphenyl)ethyl]-N'-(5,6,7,8-tetrahydro-8-quinolinyl)-1,4-benzenedimethanamine;

N,N'-bis(2-pyridinylmethyl)-1,4-(5,6,7,8-tetrahydro-8-quinolinyl)benzenedimethanamine;

N-[(2,3-dimethoxyphenyl)methyl]-N'-(2-pyridinylmethyl)-N-(5,6,7,8-tetrahydro-8-quinolinyl)-1,4-benzenedimethanamine;

N,N'-bis(2-pyridinylmethyl)-N-[1-(N"-phenyl-N"-methylureido)-4-piperidinyl]-1,3-benzenedimethanamine;

N,N'-bis(2-pyridinylmethyl)-N-[N"-p-toluenesulfonylphenylalanyl]-4-piperidinyl]-1,3-benzenedimethanamine;

N,N'-bis(2-pyridinylmethyl)-N-[1-[3-(2-chlorophenyl)-5-methyl-isoxazol-4-oyl]-4-piperidinyl]-1,3-benzenedimethanamine;

N-[(2-hydroxyphenyl)methyl]-N'-(2-pyridinylmethyl)-N-(6,7,8,9-tetrahydro-5H-cyclohepta[ bacteriapyridin-9-yl)-1,4-benzenedimethanamine;

N-[(4-cyanophenyl)methyl]-N'-(2-pyridinylmethyl)-N-(6,7,8,9-tetrahydro-5H-cyclohepta[ bacteriapyridin-9-yl)-1,4-benzenedimethanamine;

N-[(4-cyanophenyl)methyl]-N'-(2-pyridinylmethyl)-N-(5,6,7,8-tetrahydro-8-quinolinyl)-1,4-benzenedimethanamine;

N-[(4-acetamidophenyl)methyl]-N'-(2-pyridinylmethyl)-N-(5,6,7,8-tetrahydro-8-quinolinyl)-1,4-benzenedimethanamine;

N-[(4-phenoxyphenyl)methyl]-N'-(2-pyridinylmethyl)-N-(6,7,8,9-tetrahydro-5H-cyclohepta[ bacteriapyridin-9-yl)-1,4-benzenedimethanamine;

N-[(1-methyl-2-carboxamido)ethyl]-N,N'-bis(2-pyridinylmethyl)-1,3-benzenedimethanamine;

N-[(4-benzyloxyphenyl)methyl]-N'-(2-pyridinylmethyl)-N-(6,7,8,9-tetrahydro-5H-cyclohepta[bacteriapyridin-9-yl]-1,4-benzenedimethanamine;

N-[(thiophene-2-yl)methyl]-N'-(2-pyridinylmethyl)-N-(6,7,8,9-tetrahydro-5H-cyclohepta[bacteriapyridin-9-yl]-1,4-benzenedimethanamine;

N-[1-(benzyl)-3-pyrrolidinyl]-N,N'-bis(2-pyridinylmethyl)-1,3-benzenedimethanamine;

N-[[1-methyl-3-(pyrazol-3-yl)]propyl]-N,N'-bis(2-pyridinylmethyl)-1,3-benzenedimethanamine;

N-[1-(phenyl)ethyl]-N,N'-bis(2-pyridinylmethyl)-1,3-benzenedimethanamine;

N-[(3,4-methylenedioxyphenyl)methyl]-N'-(2-pyridinylmethyl)-N-(6,7,8,9-tetrahydro-5H-cyclohepta[b]pyridin-9-yl)-1,4-benzenedimethanamine;

N-[1-benzyl-3-carboxymethyl-4-piperidinyl]-N,N'-bis(2-pyridinylmethyl)-1,3-benzenedimethanamine;

N-[(3,4-methylenedioxyphenyl)methyl]-N'-(2-pyridinylmethyl)-N-(5,6,7,8-tetrahydro-8-quinolinyl)-1,4-benzenedimethanamine;

N-(3-pyridinylmethyl)-N'-(2-pyridinylmethyl)-N-(6,7,8,9-tetrahydro-5H-cyclohepta[b]pyridin-9-yl)-1,4-benzenedimethanamine;

N-[[1-methyl-2-(2-tolyl)carboxamido]ethyl]-N,N'-bis(2-pyridinylmethyl)-1,3-benzenedimethanamine;

N-[(1,5-dimethyl-2-phenyl-3-pyrazolinone-4-yl)methyl]-N'-(2-pyridinylmethyl)-N-(5,6,7,8-tetrahydro-8-quinolinyl)-1,4-benzenedimethanamine;

N-[(4-propoxyphenyl)methyl]-N'-(2-pyridinylmethyl)-N-(6,7,8,9-tetrahydro-5H-cyclohepta[b]pyridin-9-yl)-1,4-benzenedimethanamine;

N-(1-phenyl-3,5-dimethylpyrazolin-4-ylmethyl)-N'-(2-pyridinylmethyl)-N-(5,6,7,8-tetrahydro-8-quinolinyl)-1,4-benzenedimethanamine;

N-[1H-imidazol-4-ylmethyl]-N,N'-bis(2-pyridinylmethyl)-1,3-benzenedimethanamine;

N-[(3-methoxy-4,5-methylenedioxyphenyl)methyl]-N'-(2-pyridinylmethyl)-N-(6,7,8,9-tetrahydro-5H-cyclohepta[b]pyridin-9-yl)-1,4-benzenedimethanamine;

N-[(3-cyanophenyl)methyl]-N'-(2-pyridinylmethyl)-N-(6,7,8,9-tetrahydro-5H-cyclohepta[b]pyridin-9-yl)-1,4-benzenedimethanamine;

N-[(3-cyanophenyl)methyl]-N'-(2-pyridinylmethyl)-N-(5,6,7,8-tetrahydro-8-quinolinyl)-1,4-benzenedimethanamine;

N-(5-ethylthiophene-2-ylmethyl)-N'-(2-pyridinylmethyl)-N-(6,7,8,9-tetrahydro-5H-cyclohepta[b]pyridin-9-yl)-1,4-benzenedimethanamine;

N-(5-ethylthiophene-2-ylmethyl)-N'-(2-pyridinylmethyl)-N-(5,6,7,8-tetrahydro-8-quinolinyl)-1,4-benzenedimethanamine;

N-[(2,6-difluorophenyl)methyl]-N'-(2-pyridinylmethyl)-N-(6,7,8,9-tetrahydro-5H-cyclohepta[b]pyridin-9-yl)-1,4-benzenedimethanamine;

N-[(2,6-difluorophenyl)methyl]-N'-(2-pyridinylmethyl)-N-(5,6,7,8-tetrahydro-8-quinolinyl)-1,4-benzenedimethanamine;

N-[(2-difluoromethoxyphenyl)methyl]-N'-(2-pyridinylmethyl)-N-(6,7,8,9-tetrahydro-5H-cyclohepta[b]pyridin-9-yl)-1,4-benzenedimethanamine;

N-(2-difluoromethoxyphenylmethyl)-N'-(2-pyridinylmethyl)-N-(5,6,7,8-tetrahydro-8-quinolinyl)-1,4-benzenedimethanamine;

N-(1,4-benzodioxan-6-ylmethyl)-N'-(2-pyridinylmethyl)-N-(6,7,8,9-tetrahydro-5H-cyclohepta[b]pyridin-9-yl)-1,4-benzenedimethanamine;

N,N'-bis(2-pyridinylmethyl)-N-[1-(N''-phenyl-N''-methylureido)-4-piperidinyl]-1,4-benzenedimethanamine;

N,N'-bis(2-pyridinylmethyl)-N-[N''-p-toluenesulfonylphenylalanyl]-4-piperidinyl]-1,4-benzenedimethanamine;

N-[1-(3-pyridinecarboxamido)-4-piperidinyl]-N,N'-bis(2-pyridinylmethyl)-1,4-benzenedimethanamine;

N-[1-(cyclopropylcarboxamido)-4-piperidinyl]-N,N'-bis(2-pyridinylmethyl)-1,4-benzenedimethanamine;

N-[1-(1-phenylcyclopropylcarboxamido)-4-piperidinyl]-N,N'-bis(2-pyridinylmethyl)-1,4-benzenedimethanamine;

N-(1,4-benzodioxan-6-ylmethyl)-N'-(2-pyridinylmethyl)-N-(5,6,7,8-tetrahydro-8-quinolinyl)-1,4-benzenedimethanamine;

N-[1-[3-(2-chlorophenyl)-5-methyl-isoxazol-4-carboxamido]-4-piperidinyl]-N,N'-bis(2-pyridinylmethyl)-1,4-benzenedimethanamine;

N-[1-(2-thiomethylpyridine-3-carboxamido)-4-piperidinyl]-N,N'-bis(2-pyridinylmethyl)-1,4-benzenedimethanamine;

N-[(2,4-difluorophenyl)methyl]-N'-(2-pyridinylmethyl)-N-(5,6,7,8-tetrahydro-8-quinolinyl)-1,4-benzenedimethanamine;

N-(1-methylpyrrol-2-ylmethyl)-N'-(2-pyridinylmethyl)-N-(5,6,7,8-tetrahydro-8-quinolinyl)-1,4-benzenedimethanamine;

N-[(2-hydroxyphenyl)methyl]-N'-(2-pyridinylmethyl)-N-(5,6,7,8-tetrahydro-8-quinolinyl)-1,4-benzenedimethanamine;

N-[(3-methoxy-4,5-methylenedioxyphenyl)methyl]-N'-(2-pyridinylmethyl)-N-(5,6,7,8-tetrahydro-8-quinolinyl)-1,4-benzenedimethanamine;

N-(3-pyridinylmethyl)-N'-(2-pyridinylmethyl)-N-(5,6,7,8-tetrahydro-8-quinolinyl)-1,4-benzenedimethanamine;

N-[2-(N''-morpholinomethyl)-1-cyclopentyl]-N,N'-bis(2-pyridinylmethyl)-1,4-benzenedimethanamine;

N-[(1-methyl-3-piperidinyl)propyl]-N,N'-bis(2-pyridinylmethyl)-1,4-benzenedimethanamine;

N-(1-methylbenzimidazol-2-ylmethyl)-N'-(2-pyridinylmethyl)-N-(5,6,7,8-tetrahydro-8-quinolinyl)-1,4-benzenedimethanamine;

N-[1-(benzyl)-3-pyrrolidinyl]-N,N'-bis(2-pyridinylmethyl)-1,4-benzenedimethanamine;

N-[[(1-phenyl-3-(N''-morpholino)]propyl]-N,N'-bis(2-pyridinylmethyl)-1,4-benzenedimethanamine;

N-[1-(iso-propyl)-4-piperidinyl]-N,N'-bis(2-pyridinylmethyl)-1,4-benzenedimethanamine;

N-[1-(ethoxycarbonyl)-4-piperidinyl]-N'-(2-pyridinylmethyl)-N-(5,6,7,8-tetrahydro-8-quinolinyl)-1,4-benzenedimethanamine;

N-[(1-methyl-3-pyrazolyl)propyl]-N'-(2-pyridinylmethyl)-N-(5,6,7,8-tetrahydro-8-quinolinyl)-1,4-benzenedimethanamine;

N-[1-methyl-2-(N'',N''-diethylcarboxamido)ethyl]-N,N'-bis(2-pyridinylmethyl)-1,4-benzenedimethanamine;

N-[(1-methyl-2-phenylsulfonyl)ethyl]-N'-(2-pyridinylmethyl)-N-(5,6,7,8-tetrahydro-8-quinolinyl)-1,4-benzenedimethanamine;

N-[(2-chloro-4,5-methylenedioxyphenyl)methyl]-N'-(2-pyridinylmethyl)-N-(5,6,7,8-tetrahydro-8-quinolinyl)-1,4-benzenedimethanamine;

N-[1-methyl-2-[N''-(4-chlorophenyl)carboxamido]ethyl]-N'-(2-pyridinylmethyl)-N-(5,6,7,8-tetrahydro-8-quinolinyl)-1,4-benzenedimethanamine;

N-(1-acetoxyindol-3-ylmethyl)-N'-(2-pyridinylmethyl)-N-(6,7,8,9-tetrahydro-5H-cyclohepta[b]pyridin-9-yl)-1,4-benzenedimethanamine;

N-[(3-benzyloxy-4-methoxyphenyl)methyl]-N'-(2-pyridinylmethyl)-N-(6,7,8,9-tetrahydro-5H-cyclohepta[b]pyridin-9-yl)-1,4-benzenedimethanamine;

N-(3-quinolylmethyl)-N'-(2-pyridinylmethyl)-N-(5,6,7,8-tetrahydro-8-quinolinyl)-1,4-benzenedimethanamine;

N-[(8-hydroxy)-2-quinolylmethyl]-N'-(2-pyridinylmethyl)-N-(6,7,8,9-tetrahydro-5H-cyclohepta[ b]pyridin-9-yl)-1,4-benzenedimethanamine;

N-(2-quinolylmethyl)-N'-(2-pyridinylmethyl)-N-(6,7,8,9-tetrahydro-5H-cyclohepta[ b]pyridin-9-yl)-1,4-benzenedimethanamine;

N-[(4-acetamidophenyl)methyl]-N'-(2-pyridinylmethyl)-N-(6,7,8,9-tetrahydro-5H-cyclohepta[ b]pyridin-9-yl)-1,4-benzenedimethanamine;

N-[1H-imidazol-2-ylmethyl]-N,N'-bis(2-pyridinylmethyl)-1,4-benzenedimethanamine;

N-(3-quinolylmethyl)-N'-(2-pyridinylmethyl)-N-(6,7,8,9-tetrahydro-5H-cyclohepta[ b]pyridin-9-yl)-1,4-benzenedimethanamine;

N-(2-thiazolylmethyl)-N'-(2-pyridinylmethyl)-N-(6,7,8,9-tetrahydro-5H-cyclohepta[ b]pyridin-9-yl)-1,4-benzenedimethanamine;

N-(4-pyridinylmethyl)-N'-(2-pyridinylmethyl)-N-(6,7,8,9-tetrahydro-5H-cyclohepta[ b]pyridin-9-yl)-1,4-benzenedimethanamine;

N-[(5-benzyloxy)benzo[b]pyrrol-3-ylmethyl]-N,N'-bis(2-pyridinylmethyl)-1,4-benzenedimethanamine;

N-(1-methylpyrazol-2-ylmethyl)-N'-(2-pyridinylmethyl)-N-(6,7,8,9-tetrahydro-5H-cyclohepta[ b]pyridin-9-yl)-1,4-benzenedimethanamine;

N-[(4-methyl)-1H-imidazol-5-ylmethyl]-N,N'-bis(2-pyridinylmethyl)-1,4-benzenedimethanamine;

N-[[(4-dimethylamino)-1-napthalenyl]methyl]-N,N'-bis(2-pyridinylmethyl)-1,4-benzenedimethanamine;

N-[1,5-dimethyl-2-phenyl-3-pyrazolinone-4-ylmethyl]-N,N'-bis(2-pyridinylmethyl)-1,4-benzenedimethanamine;

N-[1-[(1-acetyl-2-(R)-prolinyl]-4-piperidinyl]-N-[2-(2-pyridinyl)ethyl]-N'-(2-pyridinylmethyl)-1,3-benzenedimethanamine;

N-[1-[2-acetamidobenzoyl-4-piperidinyl]-4-piperidinyl]-N-[2-(2-pyridinyl)ethyl]-N'-( 2-pyridinylmethyl)-1,3-benzenedimethanamine;

N-[(2-cyano-2-phenyl)ethyl]-N'-(2-pyridinylmethyl)-N-(6,7,8,9-tetrahydro-5H-cyclohepta[ b]pyridin-9-yl)-1,4-benzenedimethanamine;

N-[(N"-acetyltryptophanyl)-4-piperidinyl]-N-[2-(2-pyridinyl)ethyl]-N'-(2-pyridinylmethyl)-1,3-benzenedimethanamine;

N-[(N"-benzoylvalinyl)-4-piperidinyl]-N-[2-(2-pyridinyl)ethyl]-N'-(2-pyridinylmethyl)-1,3-benzenedimethanamine;

N-[(4-dimethylaminophenyl)methyl]-N'-(2-pyridinylmethyl)-N-(6,7,8,9-tetrahydro-5H-cyclohepta[ b]pyridin-9-yl)-1,4-benzenedimethanamine;

N-(4-pyridinylmethyl)-N'-(2-pyridinylmethyl)-N-(5,6,7,8-tetrahydro-8-quinolinyl)-1,4-benzenedimethanamine;

N-(1-methylbenzimadazol-2-ylmethyl)-N'-(2-pyridinylmethyl)-N-(6,7,8,9-tetrahydro-5H-cyclohepta[ b]pyridin-9-yl)-1,4-benzenedimethanamine;

N-[1-butyl-4-piperidinyl]-N-[2-(2-pyridinyl)ethyl]-N'-(2-pyridinylmethyl)-1,3-benzenedimethanamine;

N-[1-benzoyl-4-piperidinyl]-N-[2-(2-pyridinyl)ethyl]-N'-(2-pyridinylmethyl)-1,3-benzenedimethanamine;

N-[1-(benzyl)-3-pyrrolidinyl]-N-[2-(2-pyridinyl)ethyl]-N'-(2-pyridinylmethyl)-1,3-benzenedimethanamine;

N-[(1-methyl)benzo[b]pyrrol-3-ylmethyl]-N-[2-(2-pyridinyl)ethyl]-N'-(2-pyridinylmethyl)-1,3-benzenedimethanamine;

N-[1H-imidazol-4-ylmethyl]-N-[2-(2-pyridinyl)ethyl]-N'-(2-pyridinylmethyl)-1,3-benzenedimethanamine;

N-[1-(benzyl)-4-piperidinyl]-N-[2-(2-pyridinyl)ethyl]-N'-(2-pyridinylmethyl)-1,4-benzenedimethanamine;

N-[1-methylbenzimidazol-2-ylmethyl]-N-[2-(2-pyridinyl)ethyl]-N'-(2-pyridinylmethyl)-1,4-benzenedimethanamine;

N-[(2-phenyl)benzo[b]pyrrol-3-ylmethyl]-N-[2-(2-pyridinyl)ethyl]-N'-(2-pyridinylmethyl)-1,4-benzenedimethanamine;

N-[(6-methylpyridin-2-yl)methyl]-N'-(2-pyridinylmethyl)-N-(5,6,7,8-tetrahydro-8-quinolinyl)-1,4-benzenedimethanamine;

N-(3-methyl-1H-pyrazol-5-ylmethyl)-N'-(2-pyridinylmethyl)-N-(5,6,7,8-tetrahydro-8-quinolinyl)-1,3-benzenedimethanamine;

N-[(2-methoxyphenyl)methyl]-N'-(2-pyridinylmethyl)-N-(5,6,7,8-tetrahydro-8-quinolinyl)-1,3-benzenedimethanamine;

N-[(2-ethoxyphenyl)methyl]-N'-(2-pyridinylmethyl)-N-(6,7,8,9-tetrahydro-5H-cyclohepta[ b]pyridin-9-yl)-1,3-benzenedimethanamine;

N-(benzyloxyethyl)-N'-(2-pyridinylmethyl)-N-(5,6,7,8-tetrahydro-8-quinolinyl)-1,3-benzenedimethanamine;

N-[(2-ethoxy-1-naphthalenyl)methyl]-N'-(2-pyridinylmethyl)-N-(5,6,7,8-tetrahydro-8-quinolinyl)-1,3-benzenedimethanamine;

N-[(6-methylpyridin-2-yl)methyl]-N'-(2-pyridinylmethyl)-N-(5,6,7,8-tetrahydro-8-quinolinyl)-1,3-benzenedimethanamine;

1-[[4-[[(2-pyridinylmethyl)amino]methyl]phenyl]methyl] guanidine;

N-(2-pyridinylmethyl)-N-(8-methyl-8-azabicyclo[3.2.1]octan-3-yl)-1,4-benzenedimethanamine;

1-[[4-[[(2-pyridinylmethyl)amino]methyl]phenyl]methyl] homopiperazine;

1-[[3-[[(2-pyridinylmethyl)amino]methyl]phenyl]methyl] homopiperazine;

trans and cis-1-[[4-[[(2-pyridinylmethyl)amino]methyl]phenyl]methyl]-3,5-piperidinediamine;

N,N'-[1,4-Phenylenebis(methylene)]bis-4-(2-pyrimidyl) piperazine;

1-[[4-[[(2-pyridinylmethyl)amino]methyl]phenyl]methyl]-1-(2-pyridinyl)methylamine;

2-(2-pyridinyl)-5-[[(2-pyridinylmethyl)amino]methyl]-1,2,3,4-tetrahydroisoquinoline;

1-[[4-[[(2-pyridinylmethyl)amino]methyl]phenyl]methyl]-3,4-diaminopyrrolidine;

1-[[4-[[(2-pyridinylmethyl)amino]methyl]phenyl]methyl]-3,4-diacetylaminopyrrolidine;

8-[[4-[[(2-pyridinylmethyl)amino]methyl]phenyl]methyl]-2,5,8-triaza-3-oxabicyclo[4.3.0]nonane; and 8-[[4-[[(2-pyridinylmethyl)amino]methyl]phenyl]methyl]-2,5,8-triazabicyclo[4.3.0]nonane.

Methods to synthesize the compounds useful in the method of the invention are set forth in the U.S. patents and application incorporated hereinabove by reference.

As provided above, AMD3100 is an antagonist with the CXCR4 chemokine receptor (Gerlach et al., *J. Biol. Chem.* (2001) 276:14153–14160). This compound interferes with the binding of bone marrow stromal cell derived SDF-1 with CXCR4 on stem cells which leads to the release of hematopoietic stem cells from bone marrow into the circulation (Broxmeyer et al., *Blood* (2001) 98:811a (Abstract)). In a Phase 1 study at the University of Washington, Seattle, a single dose of 80 µg/kg of AMD-3100 resulted in a WBC count of 17,000/µl and a peak 6-fold increase in circulating CD34+ progenitor/stem cells at the 6 hour time point (Liles et al., *Blood* 2001 98:737a (Abstract)). In another recent study mice were injected with rhG-CSF and recombinant rat Stem Cell Factor (rrSCF) in order to mobilize large numbers of bone marrow stem cells into the circulation and then we induced a heart attack. The combination of rrSCF and rhG-CSF provides a peak number of circulating stem cells after 5 daily injections. At 27 days post surgery there was a 68% improvement in survival in the treated group versus the controls. At this time the dead tissue was replaced with regenerating myocardium and all functional parameters tested were improved compared with controls (Orlic et al., *PNAS* (2001) 98:10344–10349).

The compounds of the invention may be prepared in the form of prodrugs, i.e., protected forms which release the compounds of the invention after administration to the subject. Typically, the protecting groups are hydrolyzed in body fluids such as in the bloodstream thus releasing the active compound or are oxidized or reduced in vivo to release the active compound. A discussion of prodrugs is found in *Smith and Williams Introduction to the Principles of Drug Design*, Smith, H. J.; Wright, $2^{nd}$ ed., London (1988).

The compounds of the invention, as they are polyamines, may be administered prepared in the forms of their acid addition salts or metal complexes thereof. Suitable acid addition salts include salts of inorganic acids that are biocompatible, including HCl, HBr, sulfuric, phosphoric and the like, as well as organic acids such as acetic, propionic, butyric and the like, as well as acids containing more than one carboxyl group, such as oxalic, glutaric, adipic and the like. Typically, at physiological pH, the compounds of the invention will be in the forms of the acid addition salts. Particularly preferred are the hydrochlorides. In addition, when prepared as purified forms, the compounds may also be crystallized as the hydrates.

The compounds of the invention may be administered as sole active ingredients, as mixtures of various compounds of formula (1), and/or in admixture with additional active ingredients that are therapeutically or nutritionally useful, such as antibiotics, vitamins, herbal extracts, anti-inflammatories, glucose, antipyretics, analgesics, granulocyte-macrophage colony stimulating factor (GM-CSF), Interleukin-1 (IL-1), Interleukin-3 (IL-3), Interleukin-8 (IL-8), PIXY-321 (GM-CSF/IL-3 fusion protein), macrophage inflammatory protein, stem cell factor, thrombopoietin, growth related oncogene or chemotherapy and the like.

The compounds of the invention may be formulated for administration to animal subject using commonly understood formulation techniques well known in the art. Formulations which are suitable for particular modes of administration and for compounds of the type represented by those of formula (1) may be found in *Remington's Pharmaceutical Sciences*, latest edition, Mack Publishing Company, Easton, Pa.

Preferably, the compounds are administered by injection, most preferably by intravenous injection, but also by subcutaneous or intraperitoneal injection, and the like. Additional parenteral routes of administration include intramuscular and intraarticular injection. For intravenous or parenteral administration, the compounds are formulated in suitable liquid form with excipients as required. The compositions may contain liposomes or other suitable carriers. For injection intravenously, the solution is made isotonic using standard preparations such as Hank's solution.

Besides injection, other routes of administration may also be used. The compounds may be formulated into tablets, capsules, syrups, powders, or other suitable forms for administration orally. By using suitable excipients, these compounds may also be administered through the mucosa using suppositories or intranasal sprays. Transdermal administration can also be effected by using suitable penetrants and controlling the rate of release.

The formulation and route of administration chosen will be tailored to the individual subject, the nature of the condition to be treated in the subject, and generally, the judgment of the attending practitioner.

Suitable dosage ranges for the compounds of formula (1) vary according to these considerations, but in general, the compounds are administered in the range of about 0.1 µg/kg–5 mg/kg of body weight; preferably the range is about 1 µg/kg–300 µg/kg of body weight; more preferably about 10 µg/kg–100 µg/kg of body weight. For a typical 70-kg human subject, thus, the dosage range is from about 0.7 µg–350 mg; preferably about 700 µg–21 mg; most preferably about 700 µg–7 mg. Dosages may be higher when the compounds are administered orally or transdermally as compared to, for example, i.v. administration.

The compounds may be administered as a single bolus dose, a dose over time, as in i.v. or transdermal administration, or in multiple dosages.

In addition to direct administration to the subject, the compounds of formula (1) can be used in ex vivo treatment protocols to prepare cell cultures which are then used to replenish the blood cells of the subject. Ex vivo treatment can be conducted on autologous cells harvested from the peripheral blood or bone marrow or from allografts from matched donors. The concentration of the compound or compounds of formula (1) alone or in combination with other agents, such as macrophage inflammatory protein is a matter of routine optimization.

Subjects that will respond favorably to the method of the invention include medical and veterinary subjects generally, including human patients. Among other subjects for whom the methods of the invention is useful are cats, dogs, large animals, avians such as chickens, and the like. In general, any subject who would benefit from an elevation of progenitor cells and/or stem cells, or whose progenitor cells and/or stem cells are desirable for stem cell transplantation are appropriate for administration of the invention method.

Typical conditions which may be ameliorated or otherwise benefited by the method of the invention include hematopoietic disorders, such as aplastic anemia, leukemias, drug-induced anemias, and hematopoictic deficits from chemotherapy or radiation therapy. The method of the invention is also useful in enhancing the success of transplantation during and following immunosuppressive treatments as well as in effecting more efficient wound healing and treatment of bacterial inflammation. The method of the present invention is further useful for treating subjects who are immunocompromised or whose immune system is otherwise impaired. Typical conditions which are ameliorated or otherwise benefited by the method of the present invention, include those subjects who are infected with a retrovirus and more spe cifically who are infected with human immunodeficiency virus (HIV). The method of the invention thus targets a broad spectrum of conditions for which elevation of progenitor cells and/or stem cells in a subject would be beneficial or, where harvesting of progenitor cells and/or stem cell for subsequent stem cell transplantation would be beneficial.

The invention compounds are also administered to regenerate myocardium by mobilizing bone marrow stem cells.

Having now generally described the invention, the same will be more readily understood through reference to the following examples which are provided by way of illustration, and are not intended to be limiting of the present invention, unless specified.

EXAMPLE 1

Elevation of Mouse Progenitor Cell Levels

The effects of subcutaneous (s.c.) administration of 1,1'-[1,4-phenylene-bis(methylene)]-bis-1,4,8,11-tetraazacyclotetradecane (AMD3100) to C3H/H3 J mice on numbers of granulocyte macrophage (CFU-GM), erythroid (BFU-E), and multipotential (CFU-GEMM) progenitor cells per mL of blood were measured. Progenitors were stimulated to form colonies in vitro with the combination of 1 U/ml rhu Epo, 50 ng/ml rhu SLF, 5% $^{Vol}/_{Vol}$ pokeweed mitogen mouse spleen cell conditioned medium (PWMSCM), and 0.1 mM hemin. Plates were scored 7 days after incubation.

The time dependent effects on the number of progenitors mobilized with AMD3100 are for a single s.c. injection of 5 mg/Kg and are shown in Table 1.

TABLE 1

| | Absolute Progenitors Per ML Blood Methylcellulose Culture | | |
|---|---|---|---|
| | CFU-GM | BFU-E | CFU-GEMM |
| Control | 289.8 | 49.4 | 25.8 |
| AMD3100: 15" | 791.6 | 134.5 | 90.4 |
| AMD3100: 30" | 1805.5 | 209.3 | 113.5 |
| AMD3100: 120" | 828.7 | 102.3 | 47.6 |

To measure the dose-dependent effects, AMD3100 was administered at 1, 2.5, 5 and 10 mg/Kg via a single s.c. injection and the number of progenitors per mL of blood was measured at 1 hour post administration, and the results are shown in Table 2.

TABLE 2

| | Absolute Number Progenitors Per ML Blood Methylcellulose Culture | | |
|---|---|---|---|
| | CFU-GM | BFU-E | CFU-GEMM |
| Saline | 188.1 | 16 | 19 |
| AMD3100: 10 mg/kg | 825.6 | 120.5 | 79.8 |
| AMD3100: 5 mg/kg | 608.4 | 92.8 | 69.5 |
| AMD3100: 2.5 mg/kg | 687.6 | 98.9 | 70.6 |
| AMD3100: 1 mg/kg | 424 | 62 | 27.1 |

| Fold Change Compared to Time 0 | | | |
|---|---|---|---|
| | Progenitors Methylcellulose Culture | | |
| Time | GM | BFU-E | CFU-GEMM |
| 15" | 2.73 | 2.72 | 3.51 |
| 30" | 6.23 | 4.24 | 4.41 |
| 2' | 2.86 | 2.07 | 1.85 |

Maximum mobilization of mouse progenitors is achieved at a dose of 2.5 to 10 mg/kg AMD3100, and was observed at 0.25 to 2 hours after injection, as shown in Table 2 above.

EXAMPLE 2

Mobilization of Mouse Progenitor Cells in Combination with MIP-1α and G-CSF

The progenitor cell mobilization capacity of AMD3100 in combination with mouse (mu) macrophage inflammatory protein (MIP-1α) was tested with or without prior administration of rhu G-CSF. MIP-1α has been previously shown to mobilize progenitor cells in mice and humans (Broxmeyer, H. E., et al., Blood Cells, Molecules, and Diseases (1998) 24(2):14–30).

Groups of mice were randomized to receive control diluent (saline) or G-CSF at a dose of 2.5 μg per mouse, twice a day, for two days via s.c. injection. Eleven hours after the final injection of saline or G-CSF, the mice were divided into groups to receive MIP-1α administered I.V. at a total dose of 5 μg, AMD3100 administered s.c. at a dose of 5 mg/Kg, or a combination of both MIP-1α and AMD3100 at the same doses. One hour later, the mice were sacrificed and the number of progenitor cells per mL of blood were measured. These data are summarized in FIG. 1.

AMD3100 acts in an additive to greater than additive manner for mobilization of progenitor cells when used in combination with mouse (mu) macrophage inflammatory protein (MIP)-1α, each given 11 hours after the addition of rhu G-CSF or control diluent (saline) and 1 hour prior to assessing the blood.

EXAMPLE 3

Clinical Elevation of Progenitor Cell Levels

Five healthy human volunteers having initial white blood cell counts of 4,500–7,500 cells/mm$^3$ were used in the study. Each patient was given a single subcutaneous (s.c.) injection of 80 μg/kg AMD3100 (i.e., 1,1'-[1,4-phenylene-bis(methylene)]-bis-1,4,8,11-tetraazacyclotetradecane) in 0.9% saline, from a stock solution of 10 mg/mL AMD3100 in saline, under sterile conditions. Blood samples were obtained via catheter prior to the dose, and at various times up to 24 hours after dosing.

The blood samples were evaluated for total white blood cells, CD34 positive progenitor cells (via FACS analysis) as a percentage of total white blood cells, as well as the absolute numbers per mL and cycling status of granulocyte macrophage (CFU-GM), erythroid (BFU-E), and multipotential (CFU-GEMM) progenitor cells.

As shown in Tables 3 and 4, administration of AMD3100 caused an elevation of the white blood cell count and of CD34 positive progenitor cells in human volunteers which maximized at 6 hours post-administration.

TABLE 3

AMD3100 induced mobilization of white blood cells in individual volunteers (x 10³ WBC's).

| | | | TREATMENT | | | | | | |
|---|---|---|---|---|---|---|---|---|---|
| ID | Screen | Base-line | 30 Min | 1 Hr | 2 Hr | 4 Hr | 6 Hr | 9 Hr | Day 2 |
| P1 | 7.4 | 6.41 | 8.02 | 14.8 | 21.4 | 23.2 | 26.2 | 22.3 | 7.07 |
| P2 | 6.04 | 5.45 | 6.53 | 8.93 | 13.5 | 18.00 | 19.2 | 19.6 | 8.03 |
| P3 | 4.38 | 5.8 | 7.14 | 9.28 | ND | 18.10 | 17.9 | 18.4 | 4.98 |
| P4 | 5.08 | 5.31 | 4.37 | 7.38 | 12.4 | 14.6 | 15.8 | 13.9 | 4.98 |
| P5 | 4.53 | 5.02 | 6.08 | 8.43 | ND | 16.90 | 19.3 | 19.00 | 4.57 |

TABLE 4

AMD3100 induced mobilization of CD34 positive cells, expressed as the percentage of the total WBC's in individual volunteers.

| | | TREATMENT | | | | |
|---|---|---|---|---|---|---|
| ID | Baseline | 1 Hr | 3 Hr | 6 Hr | 9 Hr | Day 2 |
| P1 | .07 | .04 | .07 | .11 | .11 | .08 |
| P2 | .08 | .06 | .08 | .13 | .11 | .12 |
| P3 | .07 | .16 | .06 | ND | .11 | .07 |
| P4 | .05 | .07 | .09 | .09 | .1 | .1 |
| P5 | .12 | .12 | .13 | .2 | .2 | .16 |

The blood was also analyzed for AMD3100 mobilized these progenitors.

Absolute numbers of unseparated and low density (Fico-hypaque separated) nucleated cells per ml of blood, as well as the absolute numbers per ml and cycling status of granulocyte macrophage (CFU-GM), erythroid (BFU-E), and multipotential (CFU-GEMM) progenitor cells were measured in normal donors injected s.c. with AMD3100. The above parameters were assessed prior to injection and at 1, 3, 6, 9 and 24 hours after injection of AMD3100. All progenitor cell results are based on the scoring of 3 culture plates per assay per point.

For the progenitor cell numbers and cycling status, the numbers of CFU-GM, BFU-E and CFU-GEMM in methylcellulose cultures by stimulation of the cells with 1 Unit (U)/ml recombinant human (rhu) erythropoietin, 100 U/ml rhu granulocyte-macrophage colony stimulating factor (GM-CSF), 100 U/ml rhu interleukin-3 (IL-3) and 50 ng/ml rhu steel factor (SLF=stem cell factor (SCF)). The CFU-GM were also evaluated in agar cultures stimulated with 100 U/ml rhu GM-CSF and 50 ng/ml rhu SLF. For both types of assays, colonies were scored after 14 day incubation in a humidified atmosphere with 5% $CO_2$ and lowered (5%) $O_2$ tension. Cell cycling status of progenitors was measured using a high specific activity tritiated thymidine kill technique as previously described (Broxmeyer, H. E., et al., *Exp. Hematol.* (1989) 17:455–459).

The results are given first, as the mean fold change in absolute numbers of nucleated cells and progenitors at 1, 3, 6, 9 and 24 hours compared to the preinjection (=Time(T)0) counts for all five donors, as seen in Tables 5–7.

In the tables below

TABLE 5

Fold Change Compared to TIME = 0 (Average of 5 donors)

NUCLEATED CELLULARITY

| | PBL-US | | | | | PBL-LD | | | | |
|---|---|---|---|---|---|---|---|---|---|---|
| | MEAN | STD | STE | % CHG | P | MEAN | STD | STE | % CHG | P |
| T = 0 | 1.00 | 0.00 | 0.00 | 0.0% | | 1.00 | 0.00 | 0.00 | 0.0% | |
| T = 1 | 1.69 | 0.00 | 0.00 | 68.6% | 0.017 | 1.86 | 0.00 | 0.00 | 86.2% | 0.000 |
| T = 3 | 2.80 | 0.51 | 0.23 | 180.2% | 0.000 | 2.86 | 0.28 | 0.12 | 185.6% | 0.000 |
| T = 6 | 3.26 | 0.61 | 0.27 | 225.8% | 0.000 | 3.66 | 0.43 | 0.19 | 266.3% | 0.001 |
| T = 9 | 3.09 | 0.69 | 0.31 | 209.4% | 0.000 | 3.64 | 1.18 | 0.53 | 264.3% | 0.001 |
| T = 24 | 1.07 | 0.65 | 0.29 | 7.0% | 0.553 | 1.05 | 1.19 | 0.53 | 4.6% | 0.815 |

STD - Standard deviation
STE - Standard error
PEL-US - peripheral blood-unseparated
PBL-LD - peripheral blood-low density (Ficoll Separated)
P - Significance using a 2 tailed t test

TABLE 6

METHYLCELLULOSE CULTURE

| | CFU-GM | | | | | BFU-E | | | | | CFU-GEMM | | | | |
|---|---|---|---|---|---|---|---|---|---|---|---|---|---|---|---|
| | MEAN | STD | STE | % CHG | P | MEAN | STD | STE | % CHG | P | MEAN | STD | STE | % CHG | P |
| T = 0 | 1.00 | 0.00 | 0.00 | 0.0% | | 1.00 | 0.00 | 0.00 | 0.0% | | 1.00 | 0.00 | 0.00 | 0.0% | |
| T = 1 | 4.77 | 0.00 | 0.00 | 376.7% | 0.001 | 1.99 | 0.00 | 0.00 | 98.9% | 0.002 | 2.32 | 0.00 | 0.00 | 131.8% | 0.000 |
| T = 3 | 13.66 | 1.56 | 0.70 | 1266.5% | 0.001 | 3.21 | 0.50 | 0.22 | 221.3% | 0.004 | 4.33 | 0.44 | 0.20 | 332.5% | 0.000 |
| T = 6 | 21.71 | 5.78 | 2.58 | 2070.6% | 0.000 | 6.01 | 1.25 | 0.56 | 500.5% | 0.006 | 10.07 | 0.59 | 0.27 | 907.2% | 0.002 |
| T = 9 | 10.47 | 5.09 | 2.28 | 947.3% | 0.000 | 4.34 | 2.99 | 1.34 | 334.4% | 0.000 | 5.25 | 4.54 | 2.03 | 425.4% | 0.014 |
| T = 24 | 1.56 | 3.01 | 1.34 | 55.5% | 0.005 | 1.26 | 1.02 | 0.45 | 26.3% | 0.194 | 1.53 | 3.04 | 1.36 | 53.2% | 0.199 |

TABLE 7

| | AGAR CULTURE CFU-GM | | | | |
|---|---|---|---|---|---|
| | MEAN | STD | STE | % CHG | P |
| T = 0 | 1.00 | 0.00 | 0.00 | 0.0% | |
| T = 1 | 2.81 | 0.00 | 0.00 | 180.8% | 0.001 |
| T = 3 | 8.54 | 0.75 | 0.34 | 754.1% | 0.000 |
| T = 6 | 17.93 | 1.62 | 0.72 | 1692.8% | 0.000 |
| T = 9 | 10.25 | 4.57 | 2.04 | 924.9% | 0.000 |
| T = 24 | 2.08 | 2.06 | 1.03 | 108.3% | 0.073 |

The results are then shown as a fold change from T=0 levels for each individual donor, as shown in Tables 8–10.

TABLE 8

FOLD CHANGE COMPARED TO TIME = 0 for each individual patient [P]

NUCLEATED CELLULARITY

| | PBL-US | | | | | PBL-LD | | | | |
|---|---|---|---|---|---|---|---|---|---|---|
| | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 |
| T = 1 | 2.54 | 1.38 | 1.38 | 1.36 | 1.76 | 2.07 | 1.99 | 1.48 | 1.66 | 2.10 |
| T = 3 | 3.55 | 2.74 | 2.02 | 2.46 | 3.23 | 2.83 | 3.25 | 2.17 | 2.82 | 3.20 |
| T = 6 | 3.97 | 2.94 | 2.74 | 2.60 | 4.04 | 4.07 | 3.90 | 2.27 | 2.78 | 5.30 |
| T = 9 | 3.27 | 3.30 | 2.69 | 2.24 | 3.96 | 3.65 | 4.43 | 2.47 | 2.48 | 5.17 |
| T = 24 | 1.21 | 1.43 | 0.96 | 0.77 | 0.99 | 1.01 | 1.71 | 0.79 | 0.60 | 1.12 |

TABLE 9

PROGENITORS

METHYLCELLULOSE CULTURE

| | CFU-GM | | | | | BFU-E | | | | | CFU-GEMM | | | | |
|---|---|---|---|---|---|---|---|---|---|---|---|---|---|---|---|
| | P1 | P2 | P3 | P4 | P5 | P1 | P2 | P3 | P4 | P5 | P1 | P2 | P3 | P4 | P5 |
| T = 0 | 1.00 | 1.00 | 1.00 | 1.00 | 1.00 | 1.00 | 1.00 | 1.00 | 1.00 | 1.00 | 1.00 | 1.00 | 1.00 | 1.00 | 1.00 |
| T = 1 | 5.09 | 5.33 | 3.70 | 6.87 | 2.84 | 2.58 | 1.48 | 2.30 | 1.46 | 2.13 | 2.07 | 2.26 | 2.22 | 1.96 | 3.07 |
| T = 3 | 7.12 | 17.02 | 15.07 | 20.72 | 8.40 | 5.13 | 1.98 | 2.61 | 2.60 | 3.75 | 4.25 | 3.47 | 4.34 | 5.14 | 4.43 |
| T = 6 | 14.66 | 23.96 | 20.99 | 28.54 | 20.39 | 9.14 | 3.67 | 4.54 | 3.34 | 9.35 | 7.47 | 9.35 | 6.52 | 9.10 | 17.92 |
| T = 9 | 6.26 | 12.51 | 9.42 | 14.08 | 10.09 | 5.43 | 4.61 | 3.71 | 2.93 | 5.05 | 2.64 | 7.09 | 2.47 | 4.52 | 9.55 |
| T = 24 | 1.10 | 1.91 | 1.43 | 1.51 | 1.83 | 1.06 | 1.88 | 1.14 | 0.79 | 1.44 | 1.12 | 2.62 | 0.69 | 0.98 | 2.25 |

TABLE 10

| | AGAR CULTURE CFU-GM | | | | |
|---|---|---|---|---|---|
| | P1 | P2 | P3 | P4 | P5 |
| T = 0 | 1.00 | 1.00 | 1.00 | 1.00 | 1.00 |
| T = 1 | 3.05 | 3.74 | 1.67 | 2.71 | 2.87 |
| T = 3 | 8.88 | 9.49 | 7.47 | 10.46 | 6.40 |
| T = 6 | 17.77 | 24.01 | 14.04 | 13.07 | 20.75 |
| T = 9 | | 10.28 | 7.72 | 10.22 | 12.78 |
| T = 24 | | 3.69 | 1.13 | 1.30 | 2.20 |

The actual nucleated cell and progenitor cell numbers per ml of blood and the cycling status (=% progenitors in DNA synthesis (S) phase of the cell cycle) of progenitors for each of the five donors (#'s P1, P2, P3, P4, and P5) is shown in Tables 11 and 12.

TABLE 11

| | CFU-GM P1 | | BFU-E P1 | | CFU-GEMM P1 | | CFU-GM P2 | | BFU-E P2 | | CFU-GEMM P2 | |
|---|---|---|---|---|---|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 247 | 6% | 261 | 0% | 127 | 6% | 273 | 0% | 410 | 2% | 120 | 0% |
| T = 1 | 1259 | 1% | 674 | 0% | 264 | 0% | 1455 | 0% | 608 | 3% | 272 | 6% |
| T = 3 | 1760 | 1% | 1340 | 13% | 540 | 7% | 4646 | 2% | 809 | 0% | 418 | 0% |
| T = 6 | 3624 | 0% | 2388 | 0% | 949 | 0% | 6540 | 0% | 1502 | 0% | 1126 | 0% |
| T = 9 | 1547 | 2% | 1418 | 11% | 335 | 0% | 3416 | 0% | 1886 | 0% | 854 | 4% |
| T = 24 | 271 | 0% | 278 | 0% | 142 | 0% | 521 | 3% | 768 | 2% | 316 | 0% |

| | CFU-GM P3 | | BFU-E P3 | | CFU-GEMM P3 | | CFU-GM P4 | | BFU-E P4 | | CFU-GEMM P4 | |
|---|---|---|---|---|---|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 281 | 0% | 351 | 0% | 140 | 0% | 138 | 0% | 460 | 0% | 101 | 0% |
| T = 1 | 1040 | 0% | 806 | 0% | 312 | 0% | 947 | 0% | 672 | 0% | 199 | 0% |
| T = 3 | 4233 | 1% | 915 | 0% | 610 | 0% | 2857 | 5% | 1195 | 9% | 519 | 0% |
| T = 6 | 5895 | 0% | 1593 | 0% | 916 | 0% | 3936 | 0% | 1533 | 0% | 920 | 8% |
| T = 9 | 2647 | 0% | 1302 | 0% | 347 | 0% | 1942 | 0% | 1348 | 0% | 457 | 0% |
| T = 24 | 402 | 0% | 402 | 0% | 97 | 0% | 208 | 5% | 362 | 3% | 99 | 0% |

| | CFU-GM P5 | | BFU-E P5 | | CFU-GEMM P5 | |
|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 169 | 0% | 343 | 1% | 55 | 0% |
| T = 1 | 481 | 0% | 730 | 0% | 169 | 0% |
| T = 3 | 1423 | 5% | 1288 | 3% | 244 | 0% |
| T = 6 | 3454 | 0% | 3208 | 1% | 987 | 0% |
| T = 9 | 1710 | 0% | 1731 | 0% | 526 | 0% |
| T = 24 | 310 | 0% | 495 | 0% | 124 | 0% |

TABLE 12

| | AGAR Culture CFU-GM P1 | | AGAR Culture CFU-GM P2 | | AGAR Culture CFU-GM P3 | | AGAR Culture CFU-GM P4 | | AGAR Culture CFU-GM P5 | |
|---|---|---|---|---|---|---|---|---|---|---|
| | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors | Absolute # of Progenitors per ML | Cycling Status of Progenitors |
| T = 0 | 233 | 6% | 100 | 0% | 140 | 0% | 124 | 0% | 104 | 0% |
| T = 1 | 710 | 0% | 376 | 0% | 234 | 0% | 336 | 0% | 298 | 3% |
| T = 3 | 2070 | 0% | 953 | 1% | 1049 | 0% | 1299 | 0% | 664 | 0% |
| T = 6 | 4142 | 0% | 2409 | 3% | 1972 | 3% | 1623 | 0% | 2153 | 1% |
| T = 9 | | | 1032 | 0% | 1085 | 0% | 1268 | 0% | 1326 | 0% |
| T = 24 | | | 371 | 0% | 159 | 0% | 162 | 0% | 229 | 0% |

The results for all five donors were very consistent with maximal fold increases in circulating levels of progenitor cells seen 6 hours after injection of AMD3100 into the human donor subjects. Progenitors were in a slow or non-cycling state prior to and 1, 3, 6, 9 and 24 hours after injection of AMD3100.

EXAMPLE 4

Mobilized Bone Marrow Stem Cells for Myocardial Repair

Adult rats are anesthetized and a thoracotomy is performed. The descending branch of the left coronary artery is ligated and not reperfused. Within 4 to 6 hours after ligation the animals are injected with limit dilution AMD-3100 or AMD-3100 plus rhG-CSF. Control rats are not treated with the reagents. The animals are monitored at one-week intervals by echocardiography and MRI. The experiment is terminated at 2, 6 to 12 weeks post-surgery. On the day of sacrifice, the hemodynamic functions are analyzed for left ventricle-end diastolic pressure, left ventricle-developed pressure and the rate of rise and fall of left ventricle pressure. The heart is then arrested in diastole and perfused via the abdominal aorta to flush residual blood from the vascular network of the myocardium. This is followed by perfusion of the heart with 10% formalin. Several slices are made through the fixed heart and these are embedded in paraffin and sections. The sections are stained and analyzed by light microscopy to determine the size of the infarct in the treated and control animals. Tissue sections from hearts taken at 2 weeks after surgery are stained with antibodies specific for immature, developing myocyte and blood vessel proteins and analyzed by confocal microscopy. The immunohistochemical analysis involves the identification of transcription factors and surface markers expressed in early stages of myocyte development. The results of this experiment will show that when the reagent AMD-3100 is administered within hours after induction of cardiac ischemia, together with or without rhG-CSF, this reagent mobilizes bone marrow stem cells rapidly, and will result in a block to cardiac remodeling and scar formation and will lead to regeneration of the dead myocardium.

What is claimed is:

1. A method to obtain progenitor and/or stem cells from a subject
which method comprises
(a) administering to said subject a compound of the formula Z-linker-Z'     (1)

or pharmaceutically acceptable salt or prodrug form thereof
wherein Z is a cyclic polyamine containing 9–32 ring members of which 2–8 are nitrogen atoms, said nitrogen atoms separated from each other by at least 2 carbon atoms, and wherein said heterocycle may optionally contain additional heteroatoms besides nitrogen and/or may be fused to an additional ring system;
or Z is of the formula

wherein A comprises a monocyclic or bicyclic fused ring system containing at least one N and B is H or an organic moiety of 1–20 atoms,
Z' is either embodied in a form as defined by Z above, or is of the formula

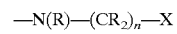

wherein each R is independently H or straight, branched or cyclic alkyl (1–6C), n is 1 or 2, and X is an aromatic ring, including heteroaromatic rings, or is a mercaptan;
"linker" represents a bond, alkylene (1–6C) or may comprise aryl, fused aryl, and/or oxygen atoms contained in an alkylene chain, and/or may contain keto groups and/or nitrogen or sulfur atoms;
in an amount effective to mobilize said progenitor and/or stem cells into the peripheral blood of said subject; followed by
(b) harvesting said progenitor and/or stem cells by apheresis.

2. The method of claim 1 wherein Z and Z' are both cyclic polyamines.

3. The method of claim 1 wherein Z and Z' are identical.

4. The method of claim 1 wherein Z is a cyclic polyamine that contains 10–24 members and contains 4 nitrogen atoms.

5. The method of claim 3 wherein Z and Z' are both 1,4,8,11-tetraazocyclotetradecane.

6. The method of claim 1 wherein the linker comprises an aromatic ring bracketed by two methylene moieties.

7. The method of claim 6 wherein the linker is 1,4-phenylene-bis-methylene.

8. The method of claim 7 wherein the compound of formula (1) is 1,1'-[1,4-phenylene-bis-(methylene)]-bis-1,4,8,11-tetraazacyclotetradecane.

9. The method of claim 1 wherein
Z is of the formula

wherein A comprises a monocyclic or bicyclic fused ring system containing at least one N and B is H or an organic moiety of 1–20 atoms.

10. The method of claim 1 wherein formula (1) is in the form of its acid addition salt.

11. The method of claim 10 wherein the acid addition salt is hydrochloride.

12. The method of claim 1 wherein the compound is administered to said subject by an intravenous or subcutaneous route.

13. The method of claim 1 wherein the compound of formula (1) is administered to said subject in the dosage range of about 0.1 µg/kg–5 mg/kg of body weight.

14. The method of claim 1 which further comprises administering macrophage inflammatory protein to said subject.

15. The method of claim 1 which further comprises administering G-CSF to said subject prior to performing said method.

16. A method to obtain progenitor and/or stem cells from a subject which method comprises
(a) administering to said subject an amount of a compound that binds to the chemokine receptor CXCR4 sufficient to mobilize said progenitor and/or stem cells into the peripheral blood of said subject; followed by
(b) harvesting said progenitor and/or stem cells by apheresis.

17. The method of claim 4 wherein Z' is

—N(R)—(CR$_2$)$_n$—X wherein each R, N and X are as defined in claim 1.

18. The method of claim 17 wherein the linker is 1,4-phenylene-bis-(methylene).

19. The method of claim 18 wherein Z' is 2-aminomethyl-pyridine.

20. The method of claim 19 wherein the compound of formula (1) is N[1,4,8,11-tetraazacyclotetradecanyl-1,4-phenylene-bis-(methylene)]-2-aminomethyl-pyridine.

21. The method of claim 1 wherein the subject is human.

22. The method of claim 16 wherein the subject is human.

* * * * *